(12) United States Patent
Christensen et al.

(10) Patent No.: US 8,728,804 B2
(45) Date of Patent: May 20, 2014

(54) POLYPEPTIDES HAVING SUCCINYL-COA: ACETOACETATE TRANSFERASE ACTIVITY AND POLYNUCLEOTIDES ENCODING SAME

(75) Inventors: Bjarke Christensen, Lyngby (DK); Peter Bjarke Olsen, Copenhagen (DK); Torsten Bak Regueira, Copenhagen (DK); Steen Troels Joergensen, Alleroed (DK); Alan Berry, Granite Bay, CA (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/882,343

(22) PCT Filed: Oct. 28, 2011

(86) PCT No.: PCT/US2011/058332
§ 371 (c)(1),
(2), (4) Date: Jul. 15, 2013

(87) PCT Pub. No.: WO2012/058566
PCT Pub. Date: May 3, 2012

(65) Prior Publication Data
US 2013/0295644 A1    Nov. 7, 2013

Related U.S. Application Data

(60) Provisional application No. 61/408,235, filed on Oct. 29, 2010.

(51) Int. Cl.
*C12N 15/00* (2006.01)
*C07H 21/04* (2006.01)

(52) U.S. Cl.
USPC ..................... 435/320.1; 536/23.2

(58) Field of Classification Search
USPC ..................... 536/23.1; 435/320.1
See application file for complete search history.

(56) References Cited

U.S. PATENT DOCUMENTS

2008/0293125 A1  11/2008  Subbian et al.
2009/0246842 A1  10/2009  Hawkins et al.

FOREIGN PATENT DOCUMENTS

| WO | 2008131286 A1 | 10/2008 |
| WO | 2009049274 A2 | 4/2009 |
| WO | 2009078973 A2 | 6/2009 |
| WO | 2009103026 A1 | 8/2009 |
| WO | 2010051527 A2 | 5/2010 |
| WO | 2010071697 A1 | 6/2010 |
| WO | 2010127303 A1 | 11/2010 |
| WO | 2011022651 A1 | 2/2011 |
| WO | 2011029166 A1 | 3/2011 |
| WO | 2011031897 A1 | 3/2011 |

OTHER PUBLICATIONS

PIR-80 database, accession No. C70079, Jul. 2004.*
PIR-80 database, accession No. B70079, Jul. 2004.*
Aldor et al, 2002, Appl Environ Microbiol 68(8), 3848-3854.
Cameron et al, 1998, Biotechnol Prog 14, 116-125.
Corthesy et al, 1997, J Biol Chem 272(41), 25659-25667.
Dayem et al, 2002, Biochemistry 41, 5193-5201.
Elferink et al, 2001 Appl Environ Microbiol 67(1), 125-132.
Falentin et al, 2010—Uniprot Acces No. D7GD28.
Froese et al, 2009, Micobiol Res 164, 1-8.
Ganzle et al, 2009, Food Microbiol 26, 712-719.
Gonzalez et al, 2008, Metab Eng 10, 234-245.
Haller et al, 2000, Biochemistry 39, 4622-4629.
Himmi et al, 2000, Appl Microbiol Biotechnol 53, 435-440.
Hofemeister et al, 2005—Uniprot Acces No. Q5NKP1.
Hosoi et al, 1979, J Ferm Tech 57(5), 418-427.
Hu et al, 2010, Bioresourse Technol 101 (21), 8477-8480.
Krooneman et al, 2002, Int J Syst Bacteriol 52, 639-646.
Siegumfeldt et al, 2000, Appl Environ Microbiol 66(6), 2330-2335.
Stols et al, 2007, Prot Expres Purif 53, 396-403.
Toru et al, 2007, Appl Microbiol Biotechnol 77(6), 1219-1224.
Wall et al, 2007, Appl Environ Microbiol 73(12), 3924-3935.
Yoshida et al, 1995—Uniprot Access No. P42316.

* cited by examiner

*Primary Examiner* — Maryam Monshipouri
(74) *Attorney, Agent, or Firm* — Eric J. Fechter

(57) ABSTRACT

The present invention relates to isolated protein complexes having succinyl-CoA:acetoacetate transferase activity, isolated polypeptide subunits thereof, and isolated polynucleotides encoding the subunits. The invention also relates to nucleic acid constructs, vectors, and host cells comprising the polynucleotides as well as methods of producing and using the polypeptides and protein complexes.

24 Claims, 6 Drawing Sheets

```
              M   G   K   V   L   S   S   S   K   E   A   A   E   L   I   R   E   G   D   T
CO    1 ATGGGGAAAG TCCTGTCGTC ATCCAAAGAA GCCGCAGAGT TAATCCGCGA AGGTGATACC
WT    1 ATGGGAAAAG TGCTGTCATC GAGTAAGGAA GCCGCGGAAC TCATTCGGGA GGGGGATACA
              L   I   A   G   G   F   G   L   C   G   I   P   E   Q   L   I   L   A   I   R
CO   61 CTGATTGCAG GTGGCTTTGG CCTGTGTGGC ATCCCGGAGC AGCTGATCCT GGCCATCCGT
WT   61 CTGATCGCGG GCGGATTCGG CCTGTGCGGA ATTCCCGAGC AGCTCATTCT GGCGATAAGG
              D   K   G   V   K   D   L   T   V   V   S   N   N   C   G   V   D   W   G
CO  121 GATAAGGGGG TTAAAGATCT GACCGTAGTT TCGAACAATT GTGGGGTTGA TGACTGGGGC
WT  121 GATAAGGGGG TAAAAGATTT AACCGTCGTC AGCAATAATT GCGGAGTTGA TGATTGGGGG
              L   G   L   L   L   A   N   K   Q   I   K   K   M   I   A   S   Y   V   G   E
CO  181 TTAGGCCTGT TACTGGCCAA TAAGCAGATC AAGAAAATGA TCGCGTCCTA CGTAGGGGAA
WT  181 CTCGGTCTGC TGCTGGCAAA CAAGCAAATC AAAAAAATGA TCGCTTCCTA CGTCGGAGAA
              N   K   I   F   E   K   Q   F   L   S   G   E   L   E   V   E   L   V   P   Q
CO  241 AACAAAATCT TCGAAAAACA GTTTCTGTCA GGGGAGTTAG AAGTGGAACT GGTACCTCAA
WT  241 AACAAAATTT TTGAAAAGCA ATTTTTAAGC GGAGAATTGG AAGTGGAATT GGTTCCCCAA
              G   T   L   E   R   I   R   A   G   G   A   G   I   P   G   F   Y   T   A
CO  301 GGTACGCTGG CGGAGCGCAT TCGGGCTGGT GGTGCAGGCA TTCCTGGCTT TTACACCGCT
WT  301 GGGACCCTCG CTGAAAGAAT CCGAGCCGGA GGAGCGGGTA TACCGGGATT TTACACAGCC
              T   G   V   G   T   S   I   A   D   G   K   E   H   K   T   F   D   G   R   T
CO  361 ACGGGTGTAG GTACGAGTAT TGCCCGATGGT AAAGAACACA AAACATTTGA TGGTCGTACC
WT  361 ACAGGCGTCG GAACATCTAT CGCTGACGGG AAAGAGCATA AAACCTTTGA CGGACGCACT
              Y   V   L   E   K   G   I   T   G   D   V   A   I   V   K   A   W   K   A   D
CO  421 TATGTGCTGG AAAAAGGCAT CACCGGTGAT GTAGCGATCG TTAAGGCTTG GAAAGCTGAT
WT  421 TATGTGTTAG AAAAAGGGAT TACTGGGGAT GTCGCCATTG TAAAAGCATG GAAAGCGGAC
              T   M   G   N   L   V   F   R   K   T   A   R   N   F   N   P   V   A   A   M
CO  481 ACAATGGGAA ACCTGGTCTT TCGTAAAACT GCCACGCAACT TCAATCCAGT TGCAGCCATG
WT  481 ACCATGGGGA ATTTAGTTTT TCGGAAAACG GCAAGAAATT TCAATCCGGT TGCCGCCATG
              A   G   K   I   T   I   A   E   A   E   I   V   E   A   G   E   L   D   P
CO  541 GCAGGCAAAA TCACGATCGC CGAGGCGGAA GAGATCGTTG AAGCAGGCGA ATTAGATCCG
WT  541 GCGGGAAAGA TCACAATTGC CGAGGCAGAA GAATTGTTG AGGCGGGAGA GCTCGATCCC
              D   H   I   H   T   P   G   I   Y   V   Q   H   V   V   L   G   T   H   E   K
CO  601 GATCACATTC ACACACCAGG CATCTATGTG CAGCATGTAG TCTTAGGTAC CCATGAAAAA
WT  601 GACCACATAC ACACGCCTGG TATTTACGTA CAGCACGTTG TGCTCGGCAC ACATGAAAAG
              R   I   E   K   R   T   V   Q   Q   A   E   G   K   E   A   A   Q   *
CO  661 CGCATCGAAA AACGCACCGT TCAGCAGGCC GAAGGGAAAG AAGCAGCCCA GTAA
WT  661 CGGATTGAAA AACGAACTGT TCAGCAAGCG GAGGGAAAGG AGGCGGCACA ATGA
```

Fig. 2

```
            M   K   E   A   R   K   R   M   V   K   R   A   V   K   E   I   K   D   G   M
CO    1 ATGAAAGAAG CACGCAAACG TATGGTTAAA CGTGCCGTCA AAGAAATCAA AGACGGGATG
WT    1 ATGAAGGAAG CCAGAAAACG AATGGTCAAA CGTGCTGTAA AGGAAATAAA AGACGGTATG
            N   V   N   L   G   I   G   M   P   T   L   V   A   N   E   I   P   E   G   V
CO   61 AATGTCAATC TGGGCATTGG CATGCCAACT CTGGTCGCCA ATGAAATTCC GGAAGGCGTG
WT   61 AACGTCAATC TTGGGATAGG GATGCCGACA CTTGTGGCAA ATGAAATACC GGAGGGCGTT
            H   V   M   L   Q   S   E   N   G   L   L   G   I   G   P   Y   P   L   D   G
CO  121 CACGTTATGT TACAGAGCGA GAACGGCCTG CTGGGTATCG GTCCTTACCC GCTGGACGGT
WT  121 CATGTGATGC TTCAATCAGA AAACGGCTTG CTTGGGATCG GCCCGTATCC GCTGGACGGA
            T   E   D   P   D   L   I   N   A   G   K   E   T   I   T   A   V   T   G   A
CO  181 ACTGAAGATC CGGATCTGAT CAATGCAGGC AAGGAGACGA TCACTGCCGT CACTGGTGCG
WT  181 ACGGAAGACC CGGATCTGAT CAATGCGGGG AAAGAAACGA TCACCGCCGT AACAGGCGCA
            S   Y   F   D   S   A   E   S   F   A   M   I   R   G   G   H   I   D   L   A
CO  241 AGCTATTTCG ATAGTGCGGA ATCGTTCGCC ATGATTCGTG GTGGGCATAT CGACCTGGCG
WT  241 TCCTATTTTG ACAGCGCAGA ATCCTTTGCG ATGATACGAG GCGGTCATAT CGACCTGGCT
            I   L   G   G   M   E   V   S   E   Q   G   D   L   A   N   W   M   I   P   G
CO  301 ATCTTAGGTG GCATGGAAGT GAGTGAACAG GGTGACCTGG CCAACTGGAT GATCCCAGGT
WT  301 ATCCTCGGGG GCATGGAGGT TTCTGAGCAA GGGGATTTGG CGAACTGGAT GATCCCGGGG
            K   M   V   K   G   M   G   G   A   M   D   L   V   N   G   A   K   R   I   V
CO  361 AAGATGGTGA AAGGTATGGG AGGAGCCATG GATCTGGTCA ACGGTGCCAA ACGTATTGTC
WT  361 AAAATGGTGA AGGGAATGGG CGGCGCTATG GATTTGGTCA ACGGGGCTAA GCGAATCGTT
            V   I   M   E   H   V   N   K   H   G   E   S   K   V   K   K   Q   C   S   L
CO  421 GTGATTATGG AACATGTGAA CAAACACGGC GAAAGTAAAG TCAAAAAGCA GTGTTCACTG
WT  421 GTCATCATGG AGCACGTCAA TAAACATGGG GAATCGAAGG TGAAAAAACA AIGCTCCCTC
            P   L   T   G   Q   K   V   V   H   R   L   I   T   D   L   A   V   F   D   F
CO  481 CCGCTGACTG GCCAGAAAGT GGTTCACCGC CTGATCACCG ACTTAGCCGT CTTTGATTTT
WT  481 CCGCTGACAG GACAGAAAGT CGTTCATCGG CTGATCACTG ATTTAGCTGT TTTTGATTTT
            D   N   G   H   M   T   L   T   E   L   Q   D   G   V   T   L   E   V   Y
CO  541 GATAACGGGC ACATGACGCT GACCGAGCTG CAGGATGGCG TCACATTGGA AGAGGTGTAC
WT  541 GATAACGGCC ATATGACACT GACTGAGCTC CAGGACGGCG TCACGCTGGA AGAGGTATAT
            E   K   T   E   A   D   F   A   V   S   Q   S   V   I   R   Q   K   S   *
CO  601 GAAAAGACAG AAGCCGATTT CGCGGTGTCC CAAAGCGTGA TCCGCCAAAA GTCTTAA
WT  601 GAGAAAACTG AAGCTGACTT CGCCGTAAGC CAGTCAGTCA TCCGGCAAAA ATCTTAA
```

POLYPEPTIDES HAVING SUCCINYL-COA:ACETOACETATE TRANSFERASE ACTIVITY AND POLYNUCLEOTIDES ENCODING SAME

CROSS REFERENCE TO RELATED APPLICATIONS

This application is a 35 U.S.C. 371 national application of PCT/US2011/58332, filed on Oct. 28, 2011, which claims priority benefit of U.S. Provisional Application No. 61/408,235, filed Oct. 29, 2010. The contents of these applications are fully incorporated herein by reference.

REFERENCE TO A SEQUENCE LISTING

This application contains a Sequence Listing in computer readable form, which is incorporated herein by reference.

REFERENCE TO A DEPOSIT OF BIOLOGICAL MATERIAL

This application contains a reference to a deposit of biological material, which deposit is incorporated herein by reference.

BACKGROUND OF THE INVENTION

1. Field of the Invention

The present invention relates to polypeptides having succinyl-CoA:acetoacetate transferase activity and polynucleotides encoding the polypeptides. The invention also relates to nucleic acid constructs, vectors, and host cells comprising the polynucleotides as well as methods of producing and using the polypeptides.

2. Description of the Related Art

Concerns related to future supply of oil have prompted research in the area of renewable energy and renewable sources of other raw materials. Biofuels, such as ethanol and bioplastics (e.g., particularly polylactic acid) are examples of products that can be made directly from agricultural sources using microorganisms. Additional desired products may then be derived using non-enzymatic chemical conversions, e.g., dehydration of ethanol to ethylene.

Polymerization of ethylene provides polyethylene, a type of plastic with a wide range of useful applications. Ethylene is traditionally produced by refined non-renewable fossil fuels, but dehydration of biologically-derived ethanol to ethylene offers an alternative route to ethylene from renewable carbon sources, i.e., ethanol from fermentation of fermentable sugars. This process has been utilized for the production of "Green Polyethylene" that—save for minute differences in the carbon isotope distribution—is identical to polyethylene produced from oil.

Similarly, isopropanol and n-propanol can be dehydrated to propylene, which in turn can be polymerized to polypropylene. As with polyethylene, using biologically-derived starting material (i.e., isopropanol or n-propanol) would result in "Green Polypropylene." However, unlike polyethylene, the production of the polyethylene starting material from renewable sources has proved challenging. Proposed efforts at propanol production have been reported in WO 2009/049274, WO 2009/103026, WO 2008/131286, and WO 2010/071697. However, no efficient fermentation process for propanol has been reported. It is clear that the successful development of a process for the biological production of propanol requires careful selection of enzymes in the metabolic pathways as well as an efficient overall metabolic engineering strategy.

It would be advantageous in the art to provide polypeptides having succinyl-CoA:acetoacetate transferase activity which may aid in improving acetoacetate and/or isopropanol production. The present invention provides polypeptides having succinyl-CoA:acetoacetate transferase activity and polynucleotides encoding the polypeptides.

SUMMARY OF THE INVENTION

The present invention relates to isolated protein complexes having succinyl-CoA:acetoacetate transferase activity, isolated polypeptide subunits thereof, and isolated polynucleotides encoding these subunits.

In one aspect, the present invention relates to isolated protein complexes having succinyl-CoA:acetoacetate transferase activity comprising a first polypeptide subunit and a second polypeptide subunit, wherein the first subunit is selected from:

(a) a polypeptide having at least 60% sequence identity to the mature polypeptide of SEQ ID NO: 3;

(b) a polypeptide encoded by a polynucleotide that hybridizes under at least low stringency conditions with the mature polypeptide coding sequence of SEQ ID NO: 1 or 2, or the full-length complementary strand thereof;

(c) a polypeptide encoded by a polynucleotide having at least 60% sequence identity to the mature polypeptide coding sequence of SEQ ID NO: 1 or 2;

(d) a variant comprising a substitution, deletion, and/or insertion of one or more (several) amino acids of the mature polypeptide of SEQ ID NO: 3; and (e) a fragment of the first subunit of (a), (b), (c), or (d) that together with the second subunit has succinyl-CoA:acetoacetate transferase activity; and wherein the second subunit is selected from:

(a) a polypeptide having at least 60% sequence identity to the mature polypeptide of SEQ ID NO: 6;

(b) a polypeptide encoded by a polynucleotide that hybridizes under at least low stringency conditions with the mature polypeptide coding sequence of SEQ ID NO: 4 or 5, or the full-length complementary strand thereof;

(c) a polypeptide encoded by a polynucleotide having at least 60% sequence identity to the mature polypeptide coding sequence of SEQ ID NO: 4 or 5;

(d) a variant comprising a substitution, deletion, and/or insertion of one or more (several) amino acids of the mature polypeptide of SEQ ID NO: 6; and (e) a fragment of the second subunit of (a), (b), (c), or (d) that together with the first subunit has succinyl-CoA:acetoacetate transferase activity.

In one aspect, the present invention relates to an isolated polypeptide subunit of a protein complex having succinyl-CoA:acetoacetate transferase activity, wherein the subunit is selected from:

(a) a polypeptide having at least 60% sequence identity to the mature polypeptide of SEQ ID NO: 3 or 6;

(b) a polypeptide encoded by a polynucleotide that hybridizes under at least low stringency conditions with the mature polypeptide coding sequence of SEQ ID NO: 1, 2, 4, or 5, or the full-length complementary strand thereof;

(c) a polypeptide encoded by a polynucleotide having at least 60% sequence identity to the mature polypeptide coding sequence of SEQ ID NO: 1, 2, 4, or 5;

(d) a variant comprising a substitution, deletion, and/or insertion of one or more (several) amino acids of the mature polypeptide of SEQ ID NO: 3 or 6; and (e) a fragment of (a), (b), (c), or (d) that together with a second subunit forms a protein complex having succinyl-CoA:acetoacetate transferase activity.

The present invention also relates to isolated polynucleotides encoding the polypeptide subunits, nucleic acid constructs, recombinant expression vectors, recombinant host cells comprising the polynucleotides, and methods of producing the polypeptides.

The present invention also relates to methods of producing isopropanol using the protein complexes, polypeptide subunits thereof, and/or polynucleotides encoding the polypeptide subunits described herein.

BRIEF DESCRIPTION OF THE FIGURES

FIG. 2 shows the genomic wild-type DNA sequence (WT), the genomic codon-optimized DNA sequence (CO), and the deduced amino acid sequence of a *Bacillus mojavensis* succinyl-CoA:acetoacetate transferase subunit A gene (scoA) (SEQ ID NOs: 1, 2, and 3, respectively).

FIG. 4 shows the genomic wild-type DNA sequence (WT), the genomic codon-optimized DNA sequence (CO), and the deduced amino acid sequence of a *Bacillus mojavensis* succinyl-CoA:acetoacetate transferase subunit B gene (scoB) (SEQ ID NOs: 4, 5, and 6, respectively).

DEFINITIONS

Figure 1:
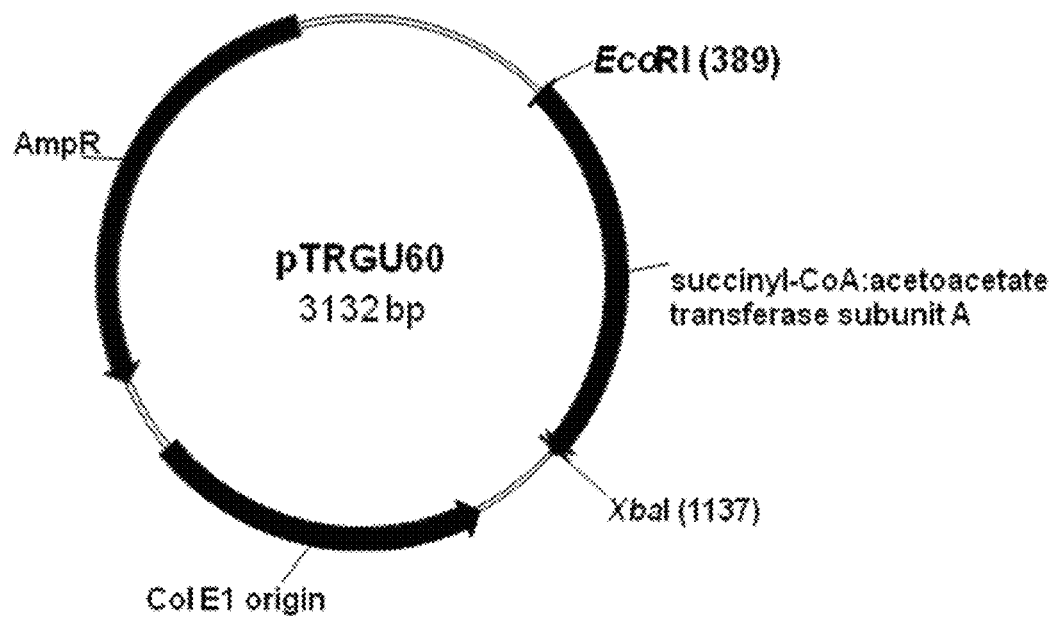
FIG. 1 shows a restriction map of pTRGU60.

Succinyl-CoA:acetoacetate transferase: The term "succinyl-CoA:acetoacetate transferase" is defined herein as an acetotransferase that catalyzes the chemical reaction of acetoacetyl-CoA and succinate to acetoacetate and succinyl-CoA (EC 2.8.3.5). The succinyl-CoA:acetoacetate transferase may be in the form of a protein complex comprising one or more (several) subunits (e.g., two heteromeric subunits) as described herein. For the purpose of the inventions described herein, succinyl-CoA:acetoacetate transferase activity may be determined according to the procedure described by L. Stols et al., 1989, *Protein Expression and Purification* 53:396-403, the content of which is hereby incorporated by reference in its entirety. For example, succinyl-CoA:acetoacetate transferase activity may be measured spectrophotometrically by monitoring the formation of the enolate anion of acetoacetyl-CoA, wherein absorbance is measured at 310 nm/30° C. over 4 minutes in an assay buffer of 67 mM lithium acetoacetate, 300 μM succinyl-CoA, and 15 mM $MgCl_2$ in 50 mM Tris, pH 9.1. One unit of succinyl-CoA:acetoacetate transferase activity equals the amount of enzyme capable of releasing 1 micromole of acetoacetate per minute at pH 9.1, 30° C.

A succinyl-CoA:acetoacetate transferase has at least 20%, e.g., at least 40%, at least 50%, at least 60%, at least 70%, at least 80%, at least 90%, at least 95%, at least 96%, at least 97%, at least 98%, at least 99%, or 100% of the succinyl-CoA:acetoacetate transferase activity of a protein complex comprising the mature polypeptide of SEQ ID NO: 3 and the mature polypeptide of SEQ ID NO: 6.

Isolated or Purified: The term "isolated" or "purified" means a polypeptide or polynucleotide that is removed from at least one component with which it is naturally associated. For example, a polypeptide may be at least 1% pure, e.g., at least 5% pure, at least 10% pure, at least 20% pure, at least 40% pure, at least 60% pure, at least 80% pure, at least 90% pure, or at least 95% pure, as determined by SDS-PAGE, and a polynucleotide may be at least 1% pure, e.g., at least 5% pure, at least 10% pure, at least 20% pure, at least 40% pure, at least 60% pure, at least 80% pure, at least 90% pure, or at least 95% pure, as determined by agarose electrophoresis.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 237 of SEQ ID NO: 3 based on the InterProScan program (The European Bioinformatics Institute) that predicts the absence of a signal peptide. In another aspect, the mature polypeptide is amino acids 1 to 218 of SEQ ID NO: 6 based on the InterProScan program (supra) that predicts the absence of a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes the referenced mature polypeptide. In one aspect, the mature polypeptide coding sequence is nucleotides 1 to 711 of SEQ ID NO: 1 or 2 based on the InterProScan program (supra) that predicts the absence of a signal peptide encoding sequence. In another aspect, the mature polypeptide coding sequence is nucleotides 1 to 654 of SEQ ID NO: 4 or 5 based on the InterProScan program (supra) that predicts the absence of a signal peptide encoding sequence.

Sequence Identity: The relatedness between two amino acid sequences or between two nucleotide sequences is described by the parameter "sequence identity". For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Fragment: The term "fragment" means a polypeptide having one or more (several) amino acids deleted from the amino and/or carboxyl terminus of a mature polypeptide. In one aspect, the fragment when combined with a second polypeptide, forms a protein complex having succinyl-CoA:acetoacetate transferase activity. In one aspect, a fragment contains at least 205 amino acid residues, e.g., at least 215 amino acid residues or at least 225 amino acid residues of SEQ ID NO: 3. In another aspect, a fragment contains at least 185 amino acid residues, e.g., at least 195 amino acid residues or at least 205 amino acid residues of SEQ ID NO: 6.

Subsequence: The term "subsequence" means a polynucleotide having one or more (several) nucleotides deleted from the 5' and/or 3' end of a mature polypeptide coding sequence. In one aspect, the subsequence encodes a fragment that when combined with a second polypeptide, forms a protein complex having succinyl-CoA:acetoacetate transferase activity. In one aspect, a subsequence contains at least 615 nucleotides, e.g., at least 645 nucleotides or at least 675 nucleotides of SEQ ID NO: 1 or 2. In another aspect, a subsequence contains at least 555 nucleotides, e.g., at least 585 nucleotides or at least 615 nucleotides of SEQ ID NO: 4 or 5.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Coding sequence: The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" means all components necessary for the expression of a polynucleotide encoding a polypeptide of the present invention. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Variant: The term "variant" means a polypeptide having succinyl-CoA:acetoacetate transferase activity, or a polypeptide of a protein complex having succinyl-CoA:acetoacetate transferase activity, wherein the polypeptide comprises an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding one or more (several) amino acids, e.g., 1-5 amino acids, adjacent to an amino acid occupying a position.

Reference to "about" a value or parameter herein includes aspects that are directed to that value or parameter per se. For example, description referring to "about X" includes the aspect "X".

As used herein and in the appended claims, the singular forms "a," "or," and "the" include plural referents unless the context clearly dictates otherwise. It is understood that the aspects of the invention described herein include "consisting" and/or "consisting essentially of" aspects.

Unless defined otherwise or clearly indicated by context, all technical and scientific terms used herein have the same meaning as commonly understood by one of ordinary skill in the art to which this invention belongs.

DETAILED DESCRIPTION OF THE INVENTION

Protein Complexes Having Succinyl-CoA:Acetoacetate Transferase Activity

The present invention relates to isolated protein complexes having succinyl-CoA:acetoacetate transferase activity. In one aspect, the isolated protein complexes are heteromeric protein complexes comprising or consisting of a first polypeptide subunit and a second polypeptide subunit. In one aspect, the isolated protein complexes having succinyl-CoA:acetoacetate transferase activity comprise or consist of a first polypeptide subunit and a second polypeptide subunit, wherein the first subunit is selected from:

(a) a polypeptide having at least 60% sequence identity to the mature polypeptide of SEQ ID NO: 3;

(b) a polypeptide encoded by a polynucleotide that hybridizes under at least low stringency conditions with the mature polypeptide coding sequence of SEQ ID NO: 1 or 2, or the full-length complementary strand thereof;

(c) a polypeptide encoded by a polynucleotide having at least 60% sequence identity to the mature polypeptide coding sequence of SEQ ID NO: 1 or 2;

(d) a variant comprising a substitution, deletion, and/or insertion of one or more (several) amino acids of the mature polypeptide of SEQ ID NO: 3; and (e) a fragment of the first subunit of (a), (b), (c), or (d) that together with the second subunit has succinyl-CoA:acetoacetate transferase activity;

and wherein the second subunit is selected from:

(a) a polypeptide having at least 60% sequence identity to the mature polypeptide of SEQ ID NO: 6;

(b) a polypeptide encoded by a polynucleotide that hybridizes under at least low stringency conditions with the mature polypeptide coding sequence of SEQ ID NO: 4 or 5, or the full-length complementary strand thereof;

(c) a polypeptide encoded by a polynucleotide having at least 60% sequence identity to the mature polypeptide coding sequence of SEQ ID NO: 6;

(d) a variant comprising a substitution, deletion, and/or insertion of one or more (several) amino acids of the mature polypeptide of SEQ ID NO: 6; and (e) a fragment of the second subunit of (a), (b), (c), or (d) that together with the first subunit has succinyl-CoA:acetoacetate transferase activity.

The present invention also relates to isolated protein complexes having succinyl-CoA:acetoacetate transferase activity comprising a first polypeptide subunit and a second polypeptide subunit, wherein the first subunit has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 3, and the second subunit has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 6. In one aspect, the first subunit comprises an amino acid sequence that differs by no more than ten amino acids, e.g., by no more than five amino acids, by no more than four amino acids, by no more than three amino acids, by no more than two amino acids, or by one amino acid from SEQ ID NO: 3, and the second subunit comprises an amino acid sequence that differs by no more than ten amino acids, e.g., by no more than five amino acids, by no more than four amino acids, by no more than three amino acids, by no more than two amino acids, or by one amino acid from SEQ ID NO: 6.

In some aspects, the first subunit comprises or consists of the mature polypeptide of SEQ ID NO: 3, an allelic variant thereof, or a fragment of the foregoing; and the second subunit comprises or consists of the mature polypeptide of SEQ ID NO: 6, an allelic variant thereof, or a fragment of the foregoing. In one aspect, the first subunit comprises or consists of the mature polypeptide of SEQ ID NO: 3, and the second subunit comprises or consists of the mature polypeptide SEQ ID NO: 6. In one aspect, the first subunit comprises or consists of SEQ ID NO: 3, and the second subunit comprises or consists of SEQ ID NO: 6.

The present invention also relates to isolated protein complexes having succinyl-CoA:acetoacetate transferase activity comprising a first polypeptide subunit and a second polypeptide subunit, wherein the first subunit is encoded by a polynucleotide that hybridizes under at least low stringency conditions, e.g., medium stringency conditions, medium-high stringency conditions, high stringency conditions, or very high stringency conditions with the mature polypeptide coding sequence of SEQ ID NO: 1 or 2, or the full-length complementary strand thereof; and the second polypeptide subunit is encoded by a polynucleotide that hybridizes under at least low stringency conditions, e.g., medium stringency conditions, medium-high stringency conditions, high stringency conditions, or very high stringency conditions with the mature polypeptide coding sequence of SEQ ID NO: 4 or 5, or the full-length complementary strand thereof (J. Sambrook, E. F. Fritsch, and T. Maniatis, 1989, *Molecular Cloning, A Laboratory Manual*, 2d edition, Cold Spring Harbor, New York).

The polynucleotide of SEQ ID NO: 1, 2, 4, or 5, or a subsequence thereof, as well as the encoded amino acid sequence of SEQ ID NO: 3 or 6, or a fragment thereof, may be used to design nucleic acid probes to identify and clone DNA encoding polypeptides having succinyl-CoA:acetoacetate transferase activity and/or protein complexes having succinyl-CoA:acetoacetate transferase activity (or subunits thereof) from strains of different genera or species according to methods well known in the art. In particular, such probes can be used for hybridization with the genomic DNA or cDNA of the genus or species of interest, following standard Southern blotting procedures, in order to identify and isolate the corresponding gene therein. Such probes can be considerably shorter than the entire sequence, but are generally at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, or at least 600 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes for polypeptides having succinyl-CoA:acetoacetate transferase activity, protein complexes having succinyl-CoA:acetoacetate transferase activity, or subunits thereof. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, 2, 4, or 5, or a subsequence thereof, the carrier material is preferably used in a Southern blot.

For purposes of the present invention, hybridization indicates that the polynucleotide hybridizes to a labeled nucleic acid probe corresponding to SEQ ID NO: 1, 2, 4, or 5; the full-length complementary strand thereof; or a subsequence of the foregoing; under very low to very high stringency conditions. Molecules to which the nucleic acid probe hybridizes under these conditions can be detected using, for example, X-ray film.

In one aspect, the nucleic acid probe is the mature polypeptide coding sequence of SEQ ID NO: 1, 2, 4, or 5. In another aspect, the nucleic acid probe is a polynucleotide that encodes the polypeptide of SEQ ID NO: 3 or 6; the mature polypeptide thereof; or a fragment of the foregoing. In another aspect, the nucleic acid probe is a polynucleotide that encodes the polypeptide of SEQ ID NO: 3. In another aspect, the nucleic acid probe is a polynucleotide that encodes the polypeptide of SEQ ID NO: 6. In another preferred aspect, the nucleic acid probe is SEQ ID NO: 1, 2, 4, or 5. In another preferred aspect, the nucleic acid probe is SEQ ID NO: 1. In another preferred aspect, the nucleic acid probe is SEQ ID NO: 2. In another preferred aspect, the nucleic acid probe is SEQ ID NO: 4. In another preferred aspect, the nucleic acid probe is SEQ ID NO: 5. In another aspect, the nucleic acid probe is the mature polypeptide coding region contained in plasmid pTRGU60 within *E. coli* DSM 24122, wherein the mature polypeptide coding region encodes a polypeptide subunit of a protein complex having succinyl-CoA:acetoacetate transferase activity. In another aspect, the nucleic acid probe is the mature polypeptide coding region contained in plasmid pTRGU61 within *E. coli* DSM 24123, wherein the mature polypeptide coding region encodes a polypeptide subunit of a protein complex having succinyl-CoA:acetoacetate transferase activity.

For long probes of at least 100 nucleotides in length, very low to very high stringency conditions are defined as prehybridization and hybridization at 42° C. in 5×SSPE, 0.3% SDS, 200 µg/mL sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), at 50° C. (low stringency), at 55° C. (medium stringency), at 60° C. (medium-high stringency), at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per mL following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The present invention also relates to isolated protein complexes having succinyl-CoA:acetoacetate transferase activity comprising a first polypeptide subunit and a second polypeptide subunit, wherein the first subunit is encoded by a polynucleotide having a sequence identity to the mature polypeptide coding sequence of SEQ ID NO: 1 or 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and the second subunit is encoded by a polynucleotide having a sequence identity to the mature polypeptide coding sequence of SEQ ID NO: 4 or 5 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The present invention also relates to isolated protein complexes having succinyl-CoA:acetoacetate transferase activity comprising a first polypeptide subunit and a second polypeptide subunit, wherein the first subunit and/or second subunit is a variant comprising a substitution, deletion, and/or insertion of one or more (several) amino acids of the mature polypeptides described herein. In one aspect, the first subunit is a variant comprising a substitution, deletion, and/or insertion of one or more (or several) amino acids of the mature polypeptide of SEQ ID NO: 3, or a homologous sequence thereof. In another aspect, the second subunit is a variant comprising a substitution, deletion, and/or insertion of one or more (or several) amino acids of the mature polypeptide of SEQ ID NO: 6, or a homologous sequence thereof. In another aspect, the first subunit is a variant comprising a substitution, deletion, and/or insertion of one or more (or several) amino acids of the mature polypeptide of SEQ ID NO: 3, or a homologous sequence thereof, and the second subunit is a variant comprising a substitution, deletion, and/or insertion of one or more (or several) amino acids of the mature polypeptide of SEQ ID NO: 6, or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide or complex thereof, alter the substrate specificity, change the pH optimum, and the like.

Essential amino acids in a parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for succinyl-CoA:acetoacetate transferase activity (e.g., when complexed with another subunit) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

In some aspects, the total number of amino acid substitutions, deletions and/or insertions of the mature polypeptide of SEQ ID NO: 3 or 6 is not more than 10, e.g., not more than 1, 2, 3, 4, 5, 6, 7, 8 or 9, such as 1, 2, 3, 4, 5, 6, 7, 8 or 9.

The polypeptide may be hybrid polypeptide in which a portion of one polypeptide is fused at the N-terminus or the C-terminus of a portion of another polypeptide. For example, the polypeptide may be a hybrid comprising a first polypeptide subunit described herein and a second polypeptide subunit described herein, wherein the polypeptide has succinyl-CoA:acetoacetate transferase activity.

The polypeptide may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The present invention also relates to isolated polypeptide subunits of the protein complexes having succinyl-CoA:acetoacetate transferase activity described herein. In one aspect, the polypeptide subunit together with a second polypeptide subunit forms a protein complex having succinyl-CoA:acetoacetate transferase activity. In one variation, the second polypeptide subunit is a heteromeric subunit (i.e., the second polypeptide subunit has a different amino acid sequence compared to the isolated polypeptide subunit). In one aspect, the isolated polypeptide subunit is selected from:

(a) a polypeptide having at least 60% sequence identity to the mature polypeptide of SEQ ID NO: 3 or 6;

(b) a polypeptide encoded by a polynucleotide that hybridizes under at least low stringency conditions with the mature polypeptide coding sequence of SEQ ID NO: 1, 2, 4, or 5, or the full-length complementary strand thereof;

(c) a polypeptide encoded by a polynucleotide having at least 60% sequence identity to the mature polypeptide coding sequence of SEQ ID NO: 1, 2, 4, or 5;

(d) a variant comprising a substitution, deletion, and/or insertion of one or more (several) amino acids of the mature polypeptide of SEQ ID NO: 3 or 6; and (e) a fragment of (a), (b), (c), or (d) that together with a second subunit forms a protein complex having succinyl-CoA:acetoacetate transferase activity.

In one aspect, the isolated polypeptide subunit has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 3 or 6. In one aspect, the isolated subunit has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 3. In one aspect, the isolated subunit has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 6. In one aspect, the isolated polypeptide subunit comprises an amino acid sequence that differs by no more than ten amino acids, e.g., by no more than five amino acids, by no more than four amino acids, by no more than three amino acids, by no more than two amino acids, or by one amino acid from SEQ ID NO: 3 or 6.

A substantially homologous polypeptide subunit may have one or more (several) amino acid substitutions, deletions and/or insertions, as described supra.

In one aspect, the isolated polypeptide subunit comprises or consists of the mature polypeptide of SEQ ID NO: 3, an allelic variant thereof, or a fragment of the foregoing. In one aspect, the isolated polypeptide subunit comprises or consists of the mature polypeptide of SEQ ID NO: 6, an allelic variant thereof, or a fragment of the foregoing. In one aspect, the isolated polypeptide subunit comprises or consists of the mature polypeptide of SEQ ID NO: 3. In one aspect, the isolated polypeptide subunit comprises or consists of the mature polypeptide SEQ ID NO: 6.

In another aspect, the isolated polypeptide subunit is a variant comprising a substitution, deletion, and/or insertion of one or more (several) amino acids of the mature polypeptide of SEQ ID NO: 3 or 6, as described supra. In some aspects, the total number of amino acid substitutions, deletions and/or insertions of the mature polypeptide of SEQ ID NO: 3 or 6 is not more than 10, e.g., not more than 1, 2, 3, 4, 5, 6, 7, 8 or 9. In another aspect, the total number of amino acid substitutions, deletions and/or insertions of the mature polypeptide of SEQ ID NO: 3 or 6 is 1, 2, 3, 4, 5, 6, 7, 8, 9, or 10.

In another aspect, the isolated polypeptide subunit is a fragment of SEQ ID NO: 3 or 6, wherein the fragment together with a second subunit forms a protein complex having succinyl-CoA:acetoacetate transferase activity. In one aspect, a fragment of SEQ ID NO: 3 contains at least 205 amino acid residues, e.g., at least 215 amino acid residues or at least 225 amino acid residues. In one aspect, a fragment of SEQ ID NO: 6 contains at least 185 amino acid residues, e.g., at least 195 amino acid residues or at least 205 amino acid residues.

In another aspect, the isolated polypeptide subunit is encoded by a polynucleotide that hybridizes under at least very low stringency conditions, e.g., low stringency conditions, medium stringency conditions, medium-high stringency conditions, high stringency conditions, or very high stringency conditions with SEQ ID NO: 1, 2, 4, or 5, the full-length complementary strand thereof, or a subsequence of the foregoing, wherein the subunit together with a second subunit forms a protein complex having succinyl-CoA:acetoacetate transferase activity (J. Sambrook, E. F. Fritsch, and T. Maniatis, 1989, supra). The subsequence may encode a polypeptide fragment wherein the fragment together with a second subunit forms a protein complex having succinyl-CoA:acetoacetate transferase activity. In one aspect, the isolated polypeptide subunit is encoded by a polynucleotide that hybridizes under at least very low stringency conditions, e.g., low stringency conditions, medium stringency conditions, medium-high stringency conditions, high stringency conditions, or very high stringency conditions with SEQ ID NO: 1 or 2, the full-length complementary strand thereof, or a subsequence of the foregoing. In one aspect, the isolated polypeptide subunit is encoded by a polynucleotide that hybridizes under at least very low stringency conditions, e.g., low stringency conditions, medium stringency conditions, medium-high stringency conditions, high stringency conditions, or very high stringency conditions with SEQ ID NO: 4 or 5, the full-length complementary strand thereof, or a subsequence of the foregoing.

A subsequence of SEQ ID NO: 1, 2, 4, 5, or a homolog thereof, is a nucleotide sequence where one or more (several) nucleotides have been deleted from the 5'- and/or 3'-end. In one aspect, a subsequence contains at least 615 nucleotides, e.g., at least 645 nucleotides or at least 675 nucleotides of SEQ ID NO: 1 or 2. In another aspect, a subsequence contains at least 555 nucleotides, e.g., at least 585 nucleotides or at least 615 nucleotides of SEQ ID NO: 4 or 5.

The polynucleotide of SEQ ID NO: 1, 2, 4, or 5; or a subsequence thereof; as well as the encoded amino acid sequence of SEQ ID NO: 5 or 6; or a fragment thereof; may be used to design nucleic acid probes to identify and clone DNA encoding the subunits from strains of different genera or species, as described supra. Such probes are encompassed by the present invention.

A genomic DNA or cDNA library prepared from such other organisms may be screened for DNA that hybridizes with the probes described above and encodes the subunits, as described supra.

In another aspect, the isolated polypeptide subunit is encoded by a polynucleotide comprising or consisting of a nucleotide sequence having a degree of sequence identity to SEQ ID NO: 1, 2, 4, or 5 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, wherein the subunit together with a second subunit forms a protein complex having succinyl-CoA:acetoacetate transferase activity. In one aspect, the isolated polypeptide subunit is encoded by a polynucleotide comprising or consisting of a nucleotide sequence having a degree of sequence identity to SEQ ID NO: 1 or 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%. In one aspect, the isolated polypeptide subunit is encoded by a polynucleotide comprising or consisting of a nucleotide sequence having a degree of sequence identity to SEQ ID NO: 4 or 5 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%.

The isolated polypeptide subunit can also include fused polypeptides or cleavable fusion polypeptides, as described supra.

Sources of Polypeptide Subunits of Protein Complexes Having Succinyl-CoA:Acetoacetate Transferase Activity Polypeptide subunits of a protein complexes having succinyl-CoA:acetoacetate transferase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a gram-positive bacterial polypeptide such as a *Bacillus*, *Clostridium*, *Enterococcus*, *Geobacillus*, *Lactobacillus*, *Lactococcus*, *Oceanobacillus*, *Staphylococcus*, *Streptococcus*, or *Streptomyces* polypeptide, or a gram-negative bacterial polypeptide such as a *Campylobacter*, *E. coli*, *Flavobacterium*, *Fusobacterium*, *Helicobacter*, *Ilyobacter*, *Neisseria*, *Pseudomonas*, *Salmonella*, or *Ureaplasma* polypeptide.

In one aspect, the polypeptide is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus mojavensis*, *Bacillus pumilus*, *Bacillus stearothermophilus*, *Bacillus subtilis*, or *Bacillus thuringiensis* polypeptide. In one aspect, the polypeptide is a *Bacillus* polypeptide, e.g., a *Bacillus mojavensis* polypeptide (such as a *Bacillus mojavensis* polypeptide of SEQ ID NO: 3 or 6.

In another aspect, the polypeptide is a *Streptococcus equisimilis*, *Streptococcus pyogenes*, *Streptococcus uberis*, or *Streptococcus equi* subsp. *Zooepidemicus* polypeptide.

In another aspect, the polypeptide is a *Streptomyces achromogenes*, *Streptomyces avermitilis*, *Streptomyces coelicolor*, *Streptomyces griseus*, or *Streptomyces lividans* polypeptide.

The polypeptide may also be a fungal polypeptide. For example, the polypeptide may be a yeast polypeptide such as a *Candida*, *Kluyveromyces*, *Pichia*, *Saccharomyces*, *Schizosaccharomyces*, or *Yarrowia* polypeptide; or a filamentous fungal polypeptide such as an *Acremonium*, *Agaricus*, *Alternaria*, *Aspergillus*, *Aureobasidium*, *Botryospaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide.

In another aspect, the polypeptide is a *Saccharomyces carlsbergensis*, *Saccharomyces cerevisiae*, *Saccharomyces*

*diastaticus, Saccharomyces douglasii, Saccharomyces kluyveri, Saccharomyces norbensis,* or *Saccharomyces oviformis* polypeptide.

In another aspect, the polypeptide is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianurn, Trichoderma koningii, Trichoderma longibrachiatum, Trichoderma reesei,* or *Trichoderma viride* polypeptide.

In another aspect, the polypeptide is a *Bacillus mojavensis* polypeptide, e.g., a *Bacillus mojavensis* polypeptide encoded by the mature polypeptide coding sequence of pTRGU60 within *E. coli* DSM 24122 or a *Bacillus mojavensis* polypeptide encoded by the mature polypeptide coding sequence of pTRGU61 within *E. coli* DSM 24123.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) using the above-mentioned probes. Techniques for isolating microorganisms from natural habitats are well known in the art. The polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Polynucleotides

The present invention also relates to isolated polynucleotides encoding the polypeptide subunits of the protein complexes described herein (e.g., an isolated polynucleotide encoding a polypeptide subunit of any aspect related to SEQ ID NO: 3 or 6).

The techniques used to isolate or clone a polynucleotide encoding a polypeptide are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Bacillus* (e.g., *Bacillus mojavensis*), or a related organism and thus, for example, may be an allelic or species variant of the polypeptide encoding region of the polynucleotide.

In one aspect, the isolated polynucleotides comprise or consist of a polynucleotide sequence having a degree of sequence identity to the mature polypeptide coding sequence of SEQ ID NO: 1 or 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which encode a polypeptide subunit of a protein complex having succinyl-CoA:acetoacetate transferase activity. In another aspect, the isolated polynucleotides comprise or consist of a polynucleotide sequence having a degree of sequence identity to the mature polypeptide coding sequence of SEQ ID NO: 4 or 5 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which encode a polypeptide subunit of a protein complex having succinyl-CoA:acetoacetate transferase activity.

Modification of a polynucleotide encoding a polypeptide subunit of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant may be constructed on the basis of the polynucleotide presented as the mature polypeptide coding sequence of SEQ ID NO: 1, 2, 4, or 5, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

In another aspect, the isolated polynucleotides hybridize under very low stringency conditions, low stringency conditions, medium stringency conditions, medium-high stringency conditions, high stringency conditions, or very high stringency conditions with the mature polypeptide coding sequence of SEQ ID NO: 1 or 2, or the full-length complementary strand thereof; or allelic variants and subsequences of the foregoing (Sambrook et al., 1989, supra), as defined herein. In one aspect, the isolated polynucleotides hybridize under very low stringency conditions, low stringency conditions, medium stringency conditions, medium-high stringency conditions, high stringency conditions, or very high stringency conditions with the mature polypeptide coding sequence of SEQ ID NO: 4 or 5, or the full-length complementary strand thereof; or allelic variants and subsequences of the foregoing, as defined herein.

In one aspect, the isolated polynucleotide comprises or consists of SEQ ID NO: 1 or 2, or the mature polypeptide coding sequence contained in plasmid pTRGU60 within *E. coli* DSM 24122 or a subsequence of SEQ ID NO: 1 or 2 that encodes a fragment of SEQ ID NO: 3, wherein the fragment is a polypeptide subunit of a protein complex having succinyl-CoA:acetoacetate transferase activity.

In another aspect, the isolated polynucleotide comprises or consists of SEQ ID NO: 4 or 5, or the mature polypeptide coding sequence contained in plasmid pTRGU61 within *E. coli* DSM 24123, or a subsequence of SEQ ID NO: 4 or 5 that encodes a fragment of SEQ ID NO: 6, wherein the fragment is a polypeptide subunit of a protein complex having succinyl-CoA:acetoacetate transferase activity.

Nucleic Acid Constructs

The present invention also relates to nucleic acid constructs comprising a polynucleotide of the present invention operably linked to one or more (several) control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a polypeptide of the present invention. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American,* 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from a gene encoding a neutral alpha-amylase in *Aspergilli* in which the untranslated leader has been replaced by an untranslated leader from a gene encoding triose phosphate isomerase in *Aspergilli*; non-limiting examples include modified promoters from the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAM111 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more (several) control sequences that direct the production of protein complex (or subunit thereof) of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any gram-positive or gram-negative bacterium. Gram-positive bacteria include, but not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The bacterial host cell may also be any *Lactobacillus* cell including, but not limited to, *L. acetotolerans*, *L. acidifarinae*, *L. acidipiscis*, *L. acidophilus*, *L. agilis*, *L. algidus*, *L. alimentarius*, *L. amylolyticus*, *L. amylophilus*, *L. amylotrophicus*, *L. amylovorus*, *L. animalis*, *L. antri*, *L. apodemi*, *L. aquaticus*, *L. arizonensis*, *L. aviarius*, *L. bavaricus*, *L. bifermentans*, *L. bobalius*, *L. brevis*, *L. buchneri*, *L. bulgaricus*, *L. cacaonum*, *L. camelliae*, *L. capillatus*, *L. carni*, *L. casei*, *L. catenaformis*, *L. cellobiosus*, *L. ceti*, *L. coleohominis*, *L. collinoides*, *L. composti*, *L. concavus*, *L. confusus*, *L. coryniformis*, *L. crispatus*, *L. crustorum*, *L. curvatus*, *L. cypricasei*, *L. delbrueckii*, *L. dextrinicus*, *L. diolivorans*, *L. divergens*, *L. durianis*, *L. equi*, *L. equicursoris*, *L. equigenerosi*, *L. fabifermentans*, *L. farciminis*, *L. farraginis*, *L. ferintoshensis*, *L. fermentum*, *L. fornicalis*, *L. fructivorans*, *L. fructosus*, *L. frumenti*, *L. fuchuensis*, *L. gallinarum*, *L. gasseri*, *L. gastricus*, *L. ghanensis*, *L. graminis*, *L. halotolerans*, *L. hammesii*, *L. hamsteri*, *L. harbinensis*, *L. hayakitensis*, *L. helveticus*, *L. heterohiochii*, *L. hilgardii*, *L. homohiochii*, *L. hordei*, *L. iners*, *L. ingluviei*, *L. intestinalis*, *L. jensenii*, *L. johnsonii*, *L. kalixensis*, *L. kandleri*, *L. kefiranofaciens*, *L. kefiranofaciens*, *L. kefirgranum*, *L. kefiri*, *L. kimchii*, *L. kisonensis*, *L. kitasatonis*, *L. kunkeei*, *L. lactis*, *L. leichmannii*, *L. lindneri*, *L. malefermentans*, *L. mali*, *L. maltaromicus*, *L. manihotivorans*, *L.*

*mindensis, L. minor, L. minutus, L. mucosae, L. murinus, L. nagelii, L. namurensis, L. nantensis, L. nodensis, L. oeni, L. oligofermentans, L. oris, L. otakiensis, L. panis, L. pantheris, L. parabrevis, L. parabuchneri, L. paracasei, L. paracollinoides, L. parafarraginis, L. parakefiri, L. paralimentarius, L. paraplantarum, L. pentosus, L. perolens, L. piscicola, L. plantarum, L. pobuzihii, L. pontis, L. psittaci, L. rapi, L. rennini, L. reuteri, L. rhamnosus, L. rimae, L. rogosae, L. rossiae, L. ruminis, L. saerimneri, L. sakei, L. salivarius, L. sanfranciscensis, L. satsumensis, L. secaliphilus, L. senmaizukei, L. sharpeae, L. siliginis, L. similis, L. sobrius, L. spicheri, L. sucicola, L. suebicus, L. sunkii, L. suntoryeus, L. taiwanensis, L. thailandensis, L. thermotolerans, L. trichodes, L. tucceti, L. uli, L. ultunensis, L. uvarum, L. vaccinostercus, L. vaginalis, L. versmoldensis, L. viridescens, L. vitulinus, L. xylosus, L. yamanashiensis, L. zeae,* and *L. zymae.* In one aspect, the bacterial host cell is *L. plantarum, L. fructivorans,* or *L. reuteri.*

In one aspect, the host cell is a member of a genus selected from *Escherichia* (e.g., *Escherichia coli*), *Lactobacillus* (e.g., *Lactobacillus plantarum, Lactobacillus fructivorans,* or *Lactobacillus reuteri*), and *Propionibacterium* (e.g., *Propionibacterium freudenreichii*).

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207), by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota (as defined by Hawksworth et al., In, Ainsworth and Bisby's *Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonaturn, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chtysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787.

Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing protein complex or polypeptide subunit thereof described herein (e.g., a protein complex or subunit thereof comprising or consisting of SEQ ID NO: 3 or 6, or any described aspect thereof). In one aspect, the present invention relates to methods of producing a polypeptide subunit described herein (e.g., a polypeptide subunit comprising or consisting of SEQ ID NO: 3 or 6, or any described aspect thereof) comprising: (a) cultivating a cell, which in its wild-type form produces the polypeptide subunit, under conditions conducive for production of the polypeptide subunit; and (b) recovering the polypeptide subunit. The present invention also relates to methods of producing a polypeptide subunit of the present invention, comprising: (a) cultivating a recombinant host cell described herein under conditions conducive for production of the polypeptide subunit; and (b) recovering the polypeptide subunit. In a one aspect, the cell is of the genus *Bacillus*. In another aspect, the cell is *Bacillus mojavensis*. In another aspect, the cell is *E. coli*. In another aspect, the cell is *E. coli* DSM 24122, or *E. coli* DSM 24123.

The present invention also relates to methods of producing a protein complex comprising a first polypeptide subunit and a second polypeptide subunit described herein, comprising: (a) cultivating a host cell, which in its wild-type form produces the first and second polypeptide subunits under conditions conducive for production of the first and second polypeptide subunits; and (b) recovering the protein complex.

In another aspect, the present invention relates to methods of producing a protein complex comprising a first polypeptide subunit and a second polypeptide subunit described herein, comprising: (a) cultivating a recombinant host cell comprising a polynucleotide encoding the first polypeptide subunit and a polynucleotide encoding the second polypeptide subunit under conditions conducive for production of the first and second polypeptide subunits; and (b) recovering the protein complex.

In another aspect, the present invention relates to methods of producing a protein complex comprising a first polypeptide subunit and a second polypeptide subunit described herein, comprising: (a) cultivating a recombinant host cell comprising a polynucleotide encoding the first polypeptide subunit and a polynucleotide encoding the second polypeptide subunit under conditions conducive for production of the first and second polypeptide subunits; (b) recovering first and second polypeptide subunits; (c) subjecting the first and second polypeptide subunits to conditions conducive to the formation of the protein complex; and (d) recovering the protein complex.

The host cells are cultivated in a nutrient medium suitable for production of the protein complexes or polypeptide subunits thereof using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The protein complexes or polypeptide subunits thereof may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The protein complexes or polypeptide subunits thereof may be recovered using methods known in the art. For example, the polypeptide may be recovered from the nutrient medium by conventional procedures including, but not limited to, centrifugation, filtration, extraction, spray-drying, evaporation, or precipitation.

The protein complexes or polypeptide subunits thereof may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989) to obtain substantially pure polypeptides.

The protein complexes or polypeptide subunits thereof may be recovered and purified according to the methods described in L. Stols et al., 1989, *Protein Expression and Purification* 53:396-403, the content of which is hereby incorporated by reference in its entirety, particularly with respect to the experimental sections therein.

In an alternative aspect, the protein complexes or polypeptide subunits thereof are not recovered, but rather a host cell of the present invention expressing the polypeptides is used as a source of the polypeptides.

Plants

The present invention also relates to isolated plants, e.g., a transgenic plant, plant part, or plant cell, comprising an isolated polynucleotide of the present invention so as to express and produce the polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide may be constructed in accordance with methods known in the art. In short, the plant or plant cell is constructed by incorporating one or more (several) expression constructs encoding a polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Mol. Biol.* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct prepared according to the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. Crossing results in the introduction of a transgene into a plant line by cross pollinating a starting line with a donor plant line. Non-limiting examples of such steps are further articulated in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention (e.g., a polypeptide subunit) comprising: (a) cultivating a transgenic plant or a plant cell comprising a polynucleotide encoding the polypeptide under conditions conducive for production of the polypeptide; and (b) recovering the polypeptide.

Removal or Reduction of Succinyl-CoA:Acetoacetate Transferase Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may be accomplished by introduction, substitution, or removal of one or more (several) nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In a particularly preferred aspect, the polynucleotide is disrupted with a selectable marker such as those described herein.

The present invention also relates to methods of inhibiting the expression in a cell of a polypeptide subunit of a protein complex having succinyl-CoA:acetoacetate transferase activity, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA (siRNAs) for inhibiting transcription. In another preferred aspect, the dsRNA is micro RNA (miRNAs) for inhibiting translation.

The present invention also relates to such double-stranded RNA (dsRNA) molecules, comprising a portion of the mature polypeptide coding sequence of SEQ ID NO: 1, 2, 4, or 5 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for the expression of native and heterologous polypeptides. Therefore, the present invention further relates to methods of producing a native or heterologous polypeptide, comprising: (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially succinyl-CoA:acetoacetate transferase subunit-free product is of particular interest in the production of eukaryotic polypeptides, in particular fungal proteins such as enzymes. The succinyl-CoA:acetoacetate transferase subunit-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product or protein complex thereof essentially free from succinyl-CoA:acetoacetate transferase activity that is produced by a method of the present invention.

Uses

The protein complexes, polypeptide subunits and nucleotides described herein may be useful for, inter alia, the production of isopropanol in recombinant host cells. Methods of using such recombinant host cells for the production of isopropanol are described in detail in copending U.S. Provisional Application No. 61/408,154, filed Oct. 29, 2010; U.S. Provisional Application No. 61/408,146, filed Oct. 29, 2010; and U.S. Provisional Application No. 61/408,138, filed Oct. 29, 2010. The content of these applications is hereby incorporated by reference in its entirety.

The present invention is further described by the following examples that should not be construed as limiting the scope of the invention.

EXAMPLES

Chemicals used as buffers and substrates were commercial products of at least reagent grade.

Media

LB plates were composed of 37 g LB agar (Sigma cat no. L3027) and double distilled water to 1 L.

LBPGS plates were composed of 37 g LB agar (Sigma cat no. L3027), 0.5% starch (Merck cat. no. 101252), 0.01 M $K_2PO_4$, 0.4% Glucose, and double distilled water to 1 L.

TY bouillon medium was composed of 20 g tryptone (Difco cat no. 211699), 5 g yeast extract (Difco cat no. 212750), $7*10^{-3}$ g ferrochloride, $1*10^{-3}$ g manganese(II)-chloride, $1.5*10^{-3}$ g magnesium sulfate, and double distilled water to 1 L.

MRS medium was obtained from Difco™, as either Difco™ Lactobacilli MRS Agar or Difco™ Lactobacilli MRS Broth, having the following compositions—Difco™ Lactobacilli MRS Agar: Proteose Peptone No. 3 (10.0 g), Beef Extract (10.0 g), Yeast Extract (5.0 g), Dextrose (20.0 g), Polysorbate 80 (1.0 g), Ammonium Citrate (2.0 g), Sodium Acetate (5.0 g), Magnesium Sulfate (0.1 g), Manganese Sulfate (0.05 g), Dipotassium Phosphate (2.0 g), Agar (15.0 g) and water to 1 L. Difco™ Lactobacilli MRS Broth: Consists of the same ingredients without the agar.

Host Strains

*Escherichia coli* SJ2: (Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. Journal of Bacteriology, 172, 4315-4321).

Example 1

Cloning of Sequences Encoding the scoA/scoB Subunits of a *B. Mojavensis* Succinyl-CoA:Acetoacetate Transferase and Construction of Vectors pTRGU60 and pTRGU61

The genomic sequence of *Bacillus mojavensis* was obtained by sequencing with a Genome Analyzer II (Illumina, San Diego, Calif., USA) using standard techniques known in the art. U.S. Pat. No. 8,327,624 reads of 72 base-pairs were assembled with Velvet version 0.7.31 in to 73 contigs and 3,913,09 base-pairs. Glimmer3 was used for gene finding resulting in 4,092 putative genes. The coding sequence (CDS) of the scoA and scoB subunits of the *B. mojavensis* succinyl-CoA:acetoacetate transferase gene were found via homology to the known scoA and scoB genes from *Bacillius subtilis*.

Figure 3:
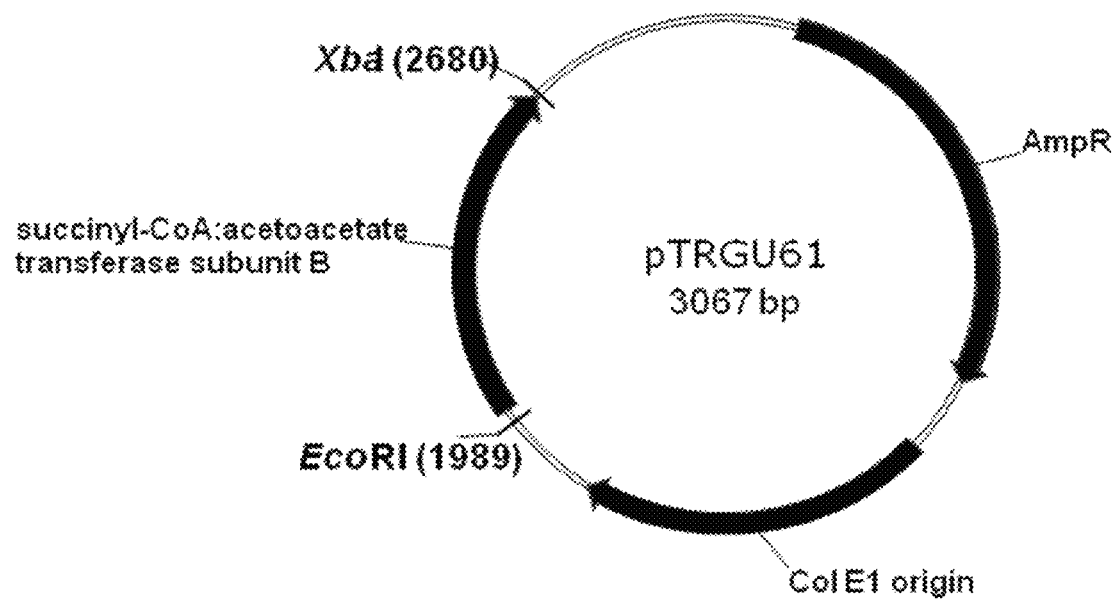
FIG. 3 shows a restriction map of pTRGU61.

The 711 bp CDS of the scoA subunit of the *B. mojavensis* succinyl-CoA:acetoacetate transferase gene and the 654 bp coding sequence of the scoB subunit of the *B. mojavensis* succinyl-CoA:acetoacetate transferase gene were optimized for expression in *E. coli* and synthetically constructed into pTRGU60 and pTRGU61, respectively. Each DNA fragment containing a codon-optimized CDS was designed with a ribosomal binding site (RBS, sequence 5'-GAAG-GAGATATACC-3') immediately prior to the start codon. The resulting sequence was then submitted to and synthesized by Geneart AG (Regenburg, Germany) and delivered in the pMA backbone vector containing the β-lactamase encoding gene blaTEM-1. When synthesized, the CDS and RBS fragment was flanked by restriction sites to facilitate subsequent cloning steps. The entire synthetic fragment containing scoA cloned into the pMA vector was EcoRI-BamHI-RBS-scoA-STOP-NotI-XbaI, resulting in pTRGU60 (FIG. 1). The entire synthetic fragment containing scoB cloned into the pMA vector was EcoRI-NotI-RBS-scoB-STOP-HindIII-XbaI, resulting in pTRGU61 (FIG. 3).

The wild-type nucleotide sequence (WT), codon-optimized nucleotide sequence (CO), and deduced amino acid sequence of the *B. mojavensis* scoA subunit of the succinyl-CoA:acetoacetate transferase gene are shown in FIG. 2 (SEQ ID NO: 1, 2, and 3, respectively). The coding sequence is 714 bp including the stop codon and the encoded predicted protein is 237 amino acids. Using the SignalP program (Nielsen et al., supra), no signal peptide in the sequence was predicted. Based on this program, the predicted mature protein contains 237 amino acids with a predicted molecular mass of 25.5 kDa and an isoelectric pH of 5.82.

The wild-type nucleotide sequence (WT), codon-optimized nucleotide sequence (CO), and deduced amino acid sequence of the *B. mojavensis* scoB subunit of the succinyl-CoA:acetoacetate transferase gene are shown in FIG. 4 (SEQ ID NO: 4, 5, and 6, respectively). The coding sequence is 657 bp including the stop codon and the encoded predicted protein is 218 amino acids. Using the SignalP program (Nielsen et al., supra), no signal peptide in the sequence was predicted.

Based on this program, the predicted mature protein contains 218 amino acids with a predicted molecular mass of 23.7 kDa and an isoelectric pH of 5.40.

Example 2

Construction and Transformation of Empty Expression Vector pTRGU88

A 2349 bp fragment containing the LacI$^q$ repressor, the trc promoter, and a multiple cloning site (MCS) was amplified from pTrc99A (E. Amann and J. Brosius, 1985, *Gene* 40(2-3), 183-190) using primers pTrcBglIItop and pTrcScaIbot shown below.

```
Primer pTrcBglIItop:
                                        (SEQ ID NO: 7)
5'-GAAGATCTATGGTGCAAAACCTTTCGCGG-3'

Primer pTrcScaIbot:
                                        (SEQ ID NO: 8)
5'-AAAAGTACTCAACCAAGTCATTCTGAG-3'
```

The PCR reaction included 12.5 pmol primer pTrcBglII-top, 12.5 pmol primer pTrcScaIbot, and 0.625 units of Platinum Pfx DNA polymerase (Invitrogen, UK). The amplification reaction was programmed for 25 cycles each at 95° C. for 2 minutes; 95° C. for 30 seconds, 42° C. for 30 seconds, and 72° C. for 2 minutes; then one cycle at 72° C. for 3 minutes. The resulting PCR product was purified with a PCR Purification Kit (Qiagen, Hilden, Germany) according to manufacturer's instructions and digested overnight at 37° C. with 5 units each of BglII (New England Biolabs, Ipswich, Mass., USA) and ScaI (New England Biolabs) (restriction sites are underlined in the above primers). The digested fragment was then purified with a PCR Purification Kit (Qiagen) according to manufacturer's instructions.

Plasmid pACYC177 (Y. K. Mok, et al., 1988, *Nucleic Acids Res.* 16(1), 356) containing a p15A origin of replication was digested at 37° C. with 5 units ScaI (New England Biolabs) and 10 units BamHI (New England Biolabs) for two hours. 10 units of calf intestine phosphatase (CIP) (New England Biolabs) were added to the digest and incubation was continued for an additional hour, resulting in a 3256 bp fragment and a 685 bp fragment. The digest mixture was run on a 1% agarose gel and the 3256 bp fragment was excised from the gel and purified using QIAquick Gel Extraction Kit (Qiagen) according to the manufacturer's instructions.

The purified 2349 bp PCR/restriction fragment was ligated into the 3256 bp restriction fragment using a Rapid Ligation Kit (F. Hoffmann-La Roche Ltd, Basel Switzerland) according to the manufacturer's instructions, resulting in pMIBa2. Plasmid pMIBa2 was digested with PstI using the standard buffer 3 and BSA as suggested by NEB, resulting in a 1078 bp PstI fragment containing the first 547 bp of blaTEM-1 (including the blaTEM-1 promoter and RBS) and a 4524 bp fragment containing the p15A origin of replication, lacIq, trc promoter, MCS, and aminoglycoside 3'-phosphotransferase gene.

Figure 5:
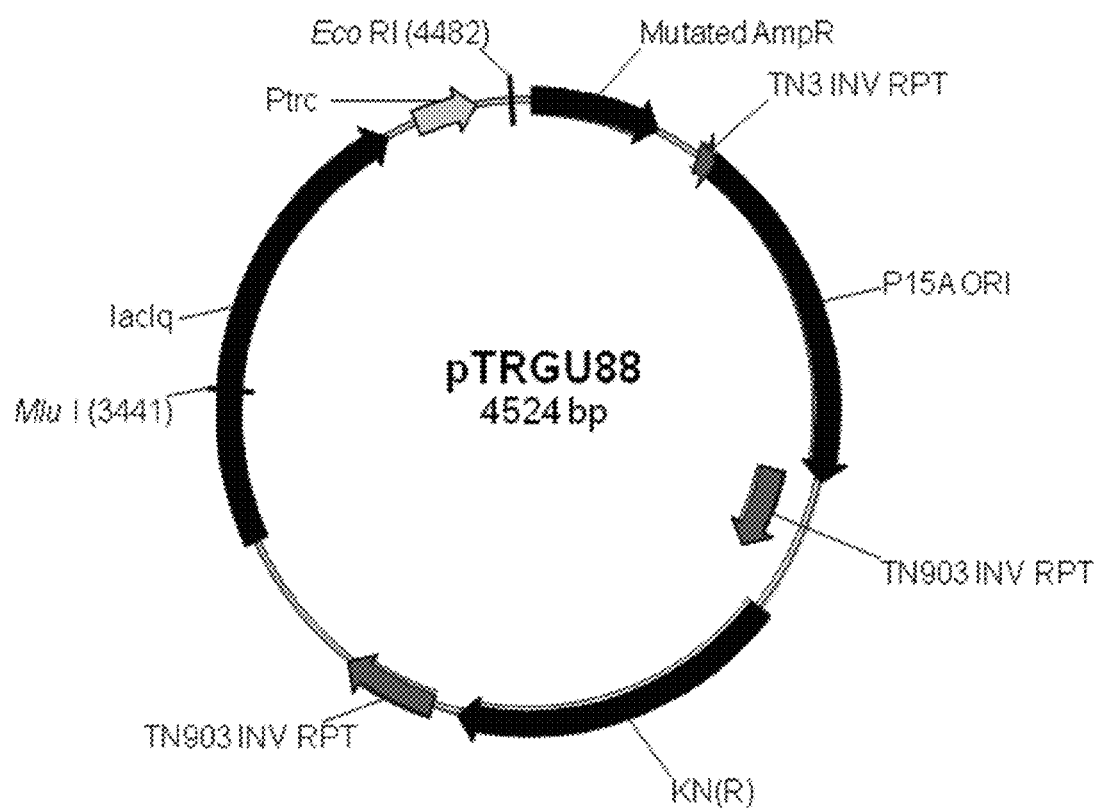
FIG. 5 shows a restriction map of pTRGU88.

The 4524 bp fragment was ligated overnight at 16° C. using T4 DNA ligase in T4 DNA ligase buffer containing 10 mM ATP (F. Hoffmann-La Roche Ltd). A 1 μl aliquot of the ligation mixture was transformed into *E. coli* SJ2 cells using electroporation. Transformants were plated onto LBPGS plates containing 20 μg/mL kanamycin and incubated at 37° C. overnight. Selected colonies were then streaked on LB plates with 200 μg/mL ampicillin and on LB plates with 20 μg/mL kanamycin. Eight transformants that were ampicillin sensitive and kanamycin resistant were isolated and streak purified on LB plates with 20 μg/mL kanamycin. Each of eight colonies was inoculated in liquid TY bouillon medium and incubated overnight at 37° C. The plasmid from each colony was isolated using a Qiaprep® Spin Miniprep Kit (Qiagen) then double digested with EcoRI and MluI. Each plasmid resulted in a correct restriction pattern of 1041 bp and 3483 bp when analyzed using the electrophoresis system "FlashGel® System" from Lonza (Basel, Switzerland). The liquid overnight culture of one transformant designated *E. coli* TRGU88 was stored in 30% glycerol at −80° C. The corresponding plasmid pTRGU88 (FIG. 5) was isolated from *E. coli* TRGU88 with a Qiaprep® Spin Miniprep Kit (Qiagen) using the manufacturer's instructions and stored at −20° C.

Example 3

Figure 6:
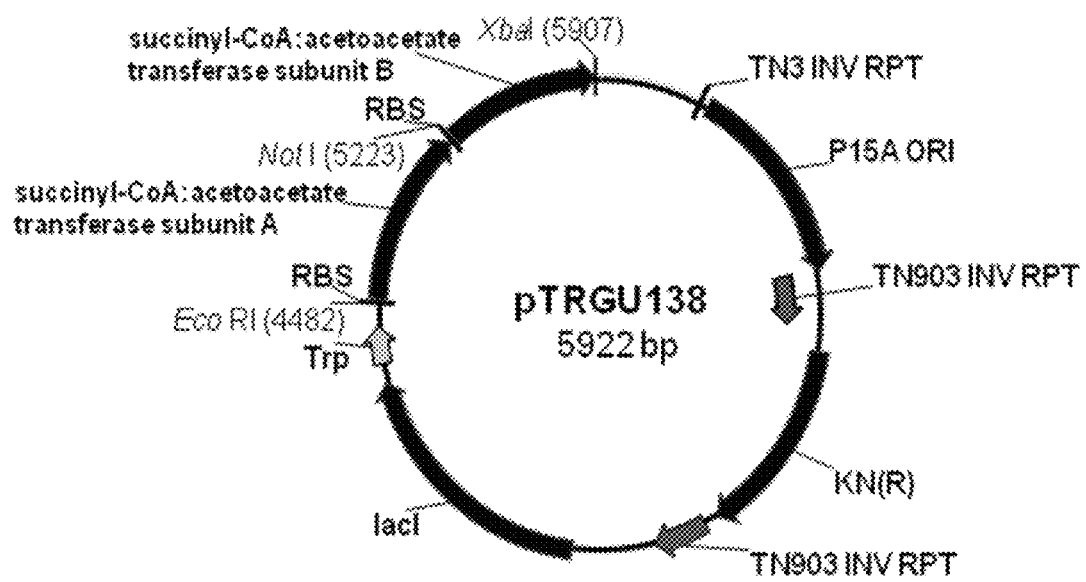
FIG. 6 shows a restriction map of pTRGU138.

Construction and Transformation of pTRGU138 Containing a Sequence Encoding Both scoA and scoB *B. Mojavensis* Succinyl-CoA:Acetoacetate Transferase Subunits Plasmids pTRGU60, pTRGU61, and pTRGU88 were digested individually with EcoRI/NotI, NotI/XbaI, and EcoRI/XbaI, respectively, and dephosphorylated with CIP using the standard methods as outlined herein. The resulting scoA fragment of pTRGU60, scoB fragment of pTRGU61, and 4497 bp fragment of pTRGU88 were each purified using gel electrophoresis as outlined herein. A three-fragment ligation of the resulting fragments was carried out using standard methods with T4 DNA ligase and T4 DNA ligase buffer containing 10 mM ATP (F. Hoffmann-La Roche Ltd), and then transformed, isolated, and stored, as outlined herein, resulting in pTRGU138 (FIG. 6) wherein the combined scoA and scoB sequence (scoAB) was flanked by the restriction sites BamHI and XbaI.

Example 4

*B. Mojavensis* Succinyl-CoA:Acetoacetate Transferase Expression and Activity Expression vectors comprising the *B. mojavensis* succinyl-CoA:acetoacetate transferase genes described above can be transformed into competent cells using standard techniques known in the art (e.g., electroporation) and confirmed by PCR.

Strains containing the *B. mojavensis* scoAB gene pair are propagated in MRS medium with 10 microgram/ml erythromycin, in stationary 2 ml cultures at 37° C. for 1 day, and the cells harvested by centrifugation.

The individual cell pellets are mechanically disrupted by treatment with glass balls, in 50 microliters of buffer (0.1 M Tris pH 7.5, 2 mM DTT) in 1.5 ml eppendorf tubes, for 5 cycles at 40 seconds in a "Bead Beater" (FastPrep FP120, BIO101 Savant) with cooling on ice in between cycles. 450 microliter of the buffer is added, cell debris is removed by centrifugation, and the supernatant is used for analysis.

The lysates are analyzed by Mass Spectrometry. Among the various proteins identified, the scoA and scoB subunits are identified with emPAI values.

Succinyl-CoA acetoacetate transferase activity is measured in the cell lysates using the following protocol. In the well of a microtiter plate 50 μl 80 mM Li-acetoacetate (Sigma A8509), 50 μl 400 μM succinyl-CoA (Sigma S1129), 50 μl buffer (200 mM Tris, 60 mM MgCl2, pH 9.1) and 50 µl cell lysate (diluted 5-20× with MilliQ water) are mixed. The acetoacetyl-CoA formed in the enzymatic reaction complexes with magnesium and is detected spectrophotometrically in a plate reader (Molecular Devices, SpectraMax Plus) by measuring absorbance at 310 nm every 20 seconds for 20 min. Blank samples without cell lysates are included. Transferase activity is calculated from the initial slope of the increase in absorbance using the equation: Activity=(Slope sample−Slope Blank)*Dilution factor. Activity is detected in the cell lysates and expressed in mOD/min.

Deposit of Biological Material

The following biological material has been deposited under the terms of the Budapest Treaty with the Deutsche Sammlung von Mikroorganismen und Zellkulturen GmbH (DSMZ), Mascheroder Weg 1 B, D-38124 Braunschweig, Germany, and given the following accession number:

| Deposit | Accession Number | Date of Deposit |
| --- | --- | --- |
| *Escherichia coli* NN059298 | DSM 24122 | Oct. 26, 2010 |
| *Escherichia coli* NN059299 | DSM 24123 | Oct. 26, 2010 |

The strain has been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The present invention may be further described by the following numbered paragraphs:

[1] An isolated protein complex having succinyl-CoA:acetoacetate transferase activity comprising a first polypeptide subunit and a second polypeptide subunit, wherein the first polypeptide subunit is selected from:

(a) a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 3;

(b) a polypeptide encoded by a polynucleotide that hybridizes under at least low stringency conditions, e.g., medium stringency conditions, medium-high stringency conditions, high stringency conditions, or very high stringency conditions with the mature polypeptide coding sequence of SEQ ID NO: 1 or 2, or the full-length complementary strand thereof;

(c) a polypeptide encoded by a polynucleotide having at least 60%, e.g., at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or 2;

(d) a variant comprising a substitution, deletion, and/or insertion of one or more (several) amino acids of the mature polypeptide of SEQ ID NO: 3; and (e) a fragment of the first subunit of (a), (b), (c), or (d) that together with the second subunit has succinyl-CoA:acetoacetate transferase activity;

and wherein the second polypeptide subunit is selected from:

(a) a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 6;

(b) a polypeptide encoded by a polynucleotide that hybridizes under at least low stringency conditions, e.g., medium stringency conditions, medium-high stringency conditions, high stringency conditions, or very high stringency conditions with the mature polypeptide coding sequence of SEQ ID NO: 4 or 5, or the full-length complementary strand thereof;

(c) a polypeptide encoded by a polynucleotide having at least 60%, e.g., at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 4 or 5;

(d) a variant comprising a substitution, deletion, and/or insertion of one or more (several) amino acids of the mature polypeptide of SEQ ID NO: 6; and (e) a fragment of the second subunit of (a), (b), (c), or (d) that together with the first subunit has succinyl-CoA:acetoacetate transferase activity.

[2] The protein complex of paragraph 1, wherein the first polypeptide subunit has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 3, and wherein the second polypeptide subunit has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 6.

[3] The protein complex of paragraph 1, wherein the first polypeptide subunit comprises or consists of SEQ ID NO: 3, and the second polypeptide subunit comprises or consists of SEQ ID NO: 6.

[4] The protein complex of paragraph 1, wherein the first polypeptide subunit comprises or consists of the mature polypeptide of SEQ ID NO: 3, and the second polypeptide subunit comprises or consists of the mature polypeptide of SEQ ID NO: 6.

[5] The protein complex of paragraph 4, wherein the mature polypeptide of SEQ ID NO: 3 is amino acids 1 to 237 of SEQ ID NO: 3, and the mature polypeptide of SEQ ID NO: 6 is amino acids 1 to 218 of SEQ ID NO: 6.

[6] The protein complex of any one of paragraphs 1-5, wherein the first polypeptide subunit is encoded by a polynucleotide that hybridizes under at least low stringency conditions, e.g., medium stringency conditions, medium-high stringency conditions, high stringency conditions, or very high stringency conditions with the mature polypeptide coding sequence of SEQ ID NO: 1 or 2, or the full-length complementary strand thereof, and wherein the second polypeptide subunit is encoded by a polynucleotide that hybridizes under at least low stringency conditions, e.g., medium stringency conditions, medium-high stringency conditions, high stringency conditions, or very high stringency conditions with the mature polypeptide coding sequence of SEQ ID NO: 4 or 5, or the full-length complementary strand thereof.

[7] The protein complex of any one of paragraphs 1-6, wherein the first polypeptide subunit is encoded by a polynucleotide having at least 60%, e.g., at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or 2,
and wherein the second polypeptide subunit is encoded by a polynucleotide having at least 60%, e.g., at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 4 or 5.

[8] The protein complex of any of paragraphs 1-7, wherein the first polypeptide subunit is a variant comprising a substitution, deletion, and/or insertion of one or more (several) amino acids of the mature polypeptide of SEQ ID NO: 3.

[9] The protein complex of any of paragraphs 1-8, wherein the second polypeptide subunit is a variant comprising a substitution, deletion, and/or insertion of one or more (several) amino acids of the mature polypeptide of SEQ ID NO: 6.

[10] The protein complex of any one of paragraphs 1-9, wherein the first polypeptide subunit is a fragment of SEQ ID NO: 3, that together with the second polypeptide subunit has succinyl-CoA:acetoacetate transferase activity.

[11] The protein complex of any one of paragraphs 1-10, wherein the second polypeptide subunit is a fragment of SEQ ID NO: 6, that together with the first polypeptide subunit has succinyl-CoA:acetoacetate transferase activity.

[12] The protein complex of any one of paragraphs 1-11, wherein the first polypeptide subunit is encoded by the polynucleotide contained in plasmid pTRGU60 which is contained in *E. coli* DSM 24122.

[13] The protein complex of any one of paragraphs 1-12, wherein the second polypeptide subunit is encoded by the polynucleotide contained in plasmid pTRGU61 which is contained in *E. coli* DSM 24123.

[14] A composition comprising the protein complex of any of paragraphs 1-13.

[15] An isolated polynucleotide encoding the protein complex of any of paragraphs 1-13.

[16] A nucleic acid construct or expression vector comprising the polynucleotide of paragraph 15 operably linked to one or more (several) control sequences that direct the production of the protein complex in an expression host.

[17] A recombinant host cell comprising the polynucleotide of paragraph 15 operably linked to one or more control sequences that direct the production of the protein complex.

[18] A method of producing a protein complex of any one of paragraphs 1-13, comprising:
(a) cultivating a host cell, which in its wild-type form produces the first and second polypeptide subunits under conditions conducive for production of the first and second polypeptide subunits; and
(b) recovering the protein complex.

[19] A method of producing a protein complex of any one of paragraphs 1-13, comprising:
(a) cultivating a recombinant host cell comprising a first polynucleotide encoding the first polypeptide subunit and a second polynucleotide encoding the second polypeptide subunit under conditions conducive for production of the first and second polypeptide subunits; and
(b) recovering the protein complex.

[20] A method of producing a protein complex of any one of paragraphs 1-13, comprising:
(a) cultivating a recombinant host cell comprising a first polynucleotide encoding the first polypeptide subunit and a second polynucleotide encoding the second polypeptide subunit under conditions conducive for production of the first and second polypeptide subunits;
(b) recovering the first and second polypeptide subunits;
(c) subjecting the first and second polypeptide subunits to conditions conducive to the formation of the protein complex; and
(d) recovering the protein complex.

[21] An isolated polypeptide subunit of a protein complex having succinyl-CoA:acetoacetate transferase activity, wherein the subunit is selected from:
(a) a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 3 or 6;
(b) a polypeptide encoded by a polynucleotide that hybridizes under at least low stringency conditions, e.g., medium stringency conditions, medium-high stringency conditions, high stringency conditions, or very high stringency conditions with the mature polypeptide coding sequence of SEQ ID NO: 1, 2, 4, or 5, or the full-length complementary strand thereof;
(c) a polypeptide encoded by a polynucleotide having at least 60%, e.g., at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1, 2, 4, or 5;
(d) a variant comprising a substitution, deletion, and/or insertion of one or more (several) amino acids of the mature polypeptide of SEQ ID NO: 3 or 6; and
(e) a fragment of (a), (b), (c), or (d) that together with a second subunit forms a protein complex having succinyl-CoA:acetoacetate transferase activity.

[22] The polypeptide subunit of paragraph 21, wherein the subunit has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 3 or 6.

[23] The polypeptide subunit of paragraph 21, wherein the subunit has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 3.

[24] The polypeptide subunit of paragraph 21, wherein the subunit has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 6.

[25] The polypeptide subunit of any one of paragraphs 21-24, wherein the subunit comprises or consists of SEQ ID NO: 3 or 6.

[26] The polypeptide subunit of any one of paragraphs 21-24, wherein the subunit comprises or consists of the mature polypeptide of SEQ ID NO: 3 or 6.

[27] The polypeptide subunit of paragraph 26, wherein the mature polypeptide of SEQ ID NO: 3 is amino acids 1 to 237 of SEQ ID NO: 3, and the mature polypeptide of SEQ ID NO: 6 is amino acids 1 to 218 of SEQ ID NO: 6.

[28] The polypeptide subunit of any one of paragraphs 21-24, wherein the subunit comprises or consists of SEQ ID NO: 3.

[29] The polypeptide subunit of any one of paragraphs 21-24, wherein the subunit comprises or consists of SEQ ID NO: 6.

[30] The polypeptide subunit of any one of paragraphs 21-29, wherein the subunit is encoded by a polynucleotide that hybridizes under at least low stringency conditions, e.g., medium stringency conditions, medium-high stringency conditions, high stringency conditions, or very high stringency conditions with the mature polypeptide coding sequence of SEQ ID NO: 1, 2, 4, or 5, or the full-length complementary strand thereof.

[31] The polypeptide subunit of any one of paragraphs 21-29, wherein the subunit is encoded by a polynucleotide that hybridizes under at least low stringency conditions, e.g., medium stringency conditions, medium-high stringency conditions, high stringency conditions, or very high stringency conditions with the mature polypeptide coding sequence of SEQ ID NO: 1 or 2, or the full-length complementary strand thereof.

[32] The polypeptide subunit of any one of paragraphs 21-29, wherein the subunit is encoded by a polynucleotide that hybridizes under at least low stringency conditions, e.g., medium stringency conditions, medium-high stringency conditions, high stringency conditions, or very high stringency conditions with the mature polypeptide coding sequence of SEQ ID NO: 4 or 5, or the full-length complementary strand thereof.

[33] The polypeptide subunit of any one of paragraphs 21-32, wherein the subunit is encoded by a polynucleotide having at least 60%, e.g., at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1, 2, 4, or 5.

[34] The polypeptide subunit of any one of paragraphs 21-32, wherein the subunit is encoded by a polynucleotide having at least 60%, e.g., at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or 2.

[35] The polypeptide subunit of any one of paragraphs 21-32, wherein the subunit is encoded by a polynucleotide having at least 60%, e.g., at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 4 or 5.

[36] The polypeptide subunit of any of paragraphs 21-35, wherein the subunit is a variant comprising a substitution, deletion, and/or insertion of one or more (several) amino acids of the mature polypeptide of SEQ ID NO: 3 or 6.

[37] The polypeptide subunit of any of paragraphs 21-35, wherein the subunit is a variant comprising a substitution, deletion, and/or insertion of one or more (several) amino acids of the mature polypeptide of SEQ ID NO: 3.

[38] The polypeptide subunit of any of paragraphs 21-35, wherein the subunit is a variant comprising a substitution, deletion, and/or insertion of one or more (several) amino acids of the mature polypeptide of SEQ ID NO: 6.

[39] The polypeptide subunit of any one of paragraphs 21-38, wherein the subunit is a fragment of SEQ ID NO: 3 or 6, that together with a second polypeptide subunit forms a protein complex having succinyl-CoA:acetoacetate transferase activity.

[40] The polypeptide subunit of any one of paragraphs 21-38, wherein the subunit is a fragment of SEQ ID NO: 3, that together with a second polypeptide subunit forms a protein complex having succinyl-CoA:acetoacetate transferase activity.

[41] The polypeptide subunit of any one of paragraphs 21-38, wherein the subunit is a fragment of SEQ ID NO: 6, that together with a second polypeptide subunit forms a protein complex having succinyl-CoA:acetoacetate transferase activity.

[42] The polypeptide subunit of any one of paragraphs 21-41, wherein the polypeptide subunit is encoded by the polynucleotide contained in plasmid pTRGU60 which is contained in *E. coli* DSM 24122 or in plasmid pTRGU61 which is contained in *E. coli* DSM 24123.

[43] The polypeptide subunit of any one of paragraphs 21-41, wherein the polypeptide subunit is encoded by the polynucleotide contained in plasmid pTRGU60 which is contained in *E. coli* DSM 24122.

[44] The polypeptide subunit of any one of paragraphs 21-41, wherein the polypeptide subunit is encoded by the polynucleotide contained in plasmid pTRGU61 which is contained in *E. coli* DSM 24123.

[45] A composition comprising the polypeptide subunit of any of paragraphs 21-44.

[46] An isolated polynucleotide encoding the polypeptide subunit of any of paragraphs 21-44.

[47] A nucleic acid construct or expression vector comprising the polynucleotide of paragraph 46 operably linked to one or more (several) control sequences that direct the production of the polypeptide subunit in an expression host.

[48] A recombinant host cell comprising the polynucleotide of paragraph 46 operably linked to one or more control sequences that direct the production of the polypeptide subunit.

[49] A method of producing the polypeptide subunit of any of paragraphs 21-44, comprising:
(a) cultivating a cell, which in its wild-type form produces the polypeptide subunit, under conditions conducive for production of the polypeptide subunit; and
(b) recovering the polypeptide subunit.

[50] A method of producing a polypeptide subunit of a protein complex having succinyl-CoA:acetoacetate transferase activity, comprising:
(a) cultivating the host cell of paragraph 48 under conditions conducive for production of the polypeptide subunit; and
(b) recovering the polypeptide subunit.

[51] A transgenic plant, plant part or plant cell transformed with a polynucleotide encoding the polypeptide subunit of any of paragraphs 21-44.

[52] A method of producing a polypeptide subunit of a protein complex having succinyl-CoA:acetoacetate transferase activity, comprising:
(a) cultivating the transgenic plant or plant cell of paragraph 51 under conditions conducive for production of the polypeptide subunit; and
(b) recovering the polypeptide subunit.

[53] A method of producing a mutant of a parent cell, comprising inactivating a polynucleotide encoding the polypeptide subunit of any of paragraphs 21-44, which results in the mutant producing less of the polypeptide subunit than the parent cell.

[54] A mutant cell produced by the method of paragraph 53.

[55] The mutant cell of paragraph 54, further comprising a gene encoding a native or heterologous protein.

[56] A method of producing a protein, comprising:
(a) cultivating the mutant cell of paragraph 54 or 56 under conditions conducive for production of the protein; and
(b) recovering the protein.

[57] A double-stranded inhibitory RNA (dsRNA) molecule comprising a subsequence of the polynucleotide of paragraph 46, wherein optionally the dsRNA is an siRNA or an miRNA molecule.

[58] The double-stranded inhibitory RNA (dsRNA) molecule of paragraph 57, which is about 15, 16, 17, 18, 19, 20, 21, 22, 23, 24, 25 or more duplex nucleotides in length.

[59] A method of inhibiting the expression in a cell of a polypeptide subunit of a protein complex having succinyl-CoA:acetoacetate transferase activity, comprising administering to the cell or expressing in the cell the double-stranded inhibitory RNA (dsRNA) molecule of paragraph 57 or 58.

[60] A cell produced by the method of paragraph 59.

[61] The cell of paragraph 60, further comprising a gene encoding a native or heterologous protein.

[62] A method of producing a protein, comprising:
(a) cultivating the cell of paragraph 60 or 61 under conditions conducive for production of the protein; and
(b) recovering the protein.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A nucleic acid construct or expression vector, comprising a polynucleotide encoding a protein complex having succinyl-CoA:acetoacetate transferase activity operably linked to one or more heteroloqous control sequences that direct the production of the protein complex in an expression host,
   wherein the complex comprises
   a first polypeptide subunit selected from:
   (a) a polypeptide having at least 97% sequence identity to SEQ ID NO: 3;
   (b) a polypeptide encoded by a polynucleotide that hybridizes under at least very high stringency conditions with the full-length complementary strand of SEQ ID NO: 1 or 2; and
   (c) a polypeptide encoded by a polynucleotide having at least 97% sequence identity to SEQ ID NO: 1 or 2;
   and a second polypeptide subunit selected from:
   (a) a polypeptide having at least 97% sequence identity to SEQ ID NO: 6;
   (b) a polypeptide encoded by a polynucleotide that hybridizes under at least very high stringency conditions with the full-length complementary strand of SEQ ID NO: 4 or 5; and
   (c) a polypeptide encoded by a polynucleotide having at least 97% sequence identity to SEQ ID NO: 4 or 5.

2. A nucleic acid construct or expression vector comprising a polynucleotide encoding the first or second polypeptide subunit of the protein complex of claim 1 operably linked to one or more heterologous control sequences that direct the production of said subunit in an expression host.

3. A recombinant host cell comprising the nucleic acid construct or expression vector of claim 1.

4. The recombinant host cell of claim 3, wherein the host cell is prokaryotic.

5. The recombinant host cell of claim 4, wherein the host cell is a member of a genus selected from *Bacillus, Clostridium, Enterococcus, Geobacillus, Lactobacillus, Lactococcus, Oceanobacillus, Propionibacterium, Staphylococcus, Streptococcus, Streptomyces, Campylobacter, Escherichia, Flavobacterium, Fusobacterium, Helicobacter, Ilyobacter, Neisseria, Pseudomonas, Salmonella,* and *Ureaplasma.*

6. The recombinant host cell of claim 5, wherein the host cell is a member of the *Lactobacillus* genus or *Propionibacterium* genus.

7. The nucleic acid construct or expression vector of claim 1, wherein the first polypeptide subunit has at least 97% sequence identity to SEQ ID NO: 3, and wherein the second polypeptide subunit has at least 97% sequence identity to SEQ ID NO: 6.

8. The nucleic acid construct or expression vector of claim 1, wherein the first polypeptide subunit has at least 99% sequence identity to SEQ ID NO: 3, and wherein the second polypeptide subunit has at least 99% sequence identity to SEQ ID NO: 6.

9. The nucleic acid construct or expression vector of claim 1, wherein the first polypeptide subunit comprises or consists of SEQ ID NO: 3, and the second polypeptide subunit comprises or consists of SEQ ID NO: 6.

10. The nucleic acid construct or expression vector of claim 1, wherein the first polypeptide subunit is encoded by a polynucleotide that hybridizes under at least very high stringency conditions with the full-length complementary strand of SEQ ID NO: 1 or 2,
and wherein the second polypeptide subunit is encoded by a polynucleotide that hybridizes under at least very high stringency conditions with the full-length complementary strand of SEQ ID NO: 4 or 5.

11. The nucleic acid construct or expression vector of claim 1, wherein the first polypeptide subunit is encoded by a polynucleotide having at least 97% sequence identity to SEQ ID NO: 1 or 2,
and wherein the second polypeptide subunit is encoded by a polynucleotide having at least 97% sequence identity to SEQ ID NO: 4 or 5.

12. The nucleic acid construct or expression vector of claim 1, wherein the first polypeptide subunit is encoded by a polynucleotide having at least at least 99% sequence identity to SEQ ID NO: 1 or 2,
and wherein the second polypeptide subunit is encoded by a polynucleotide having of 90% at least 99% sequence identity to SEQ ID NO: 4 or 5.

13. The nucleic acid construct or expression vector of claim 1, wherein the first polypeptide subunit is encoded by the polynucleotide contained in plasmid pTRGU60 which is contained in *E. coli* DSM 24122.

14. The nucleic acid construct or expression vector of claim 1, wherein the second polypeptide subunit is encoded by the polynucleotide contained in plasmid pTRGU61 which is contained in *E. coli* DSM 24123.

15. The nucleic acid construct or expression vector of claim 2, wherein the polynucleotide encodes a polypeptide subunit having at least 97% sequence identity to SEQ ID NO: 3.

16. The nucleic acid construct or expression vector of claim 2, wherein the polynucleotide encodes a polypeptide subunit having at least 99% sequence identity to SEQ ID NO: 3.

17. The nucleic acid construct or expression vector of claim 2, wherein the polynucleotide encodes a polypeptide subunit comprising or consisting of SEQ ID NO: 3.

18. The nucleic acid construct or expression vector of claim 2, wherein the polynucleotide encodes a polypeptide subunit having at least 97% sequence identity to SEQ ID NO: 6.

19. The nucleic acid construct or expression vector of claim 2, wherein the polynucleotide encodes a polypeptide subunit having at least 99% sequence identity to SEQ ID NO: 6.

20. The nucleic acid construct or expression vector of claim 2, wherein the polynucleotide encodes a polypeptide subunit comprising or consisting of SEQ ID NO: 6.

21. A recombinant host cell comprising the nucleic acid construct or expression vector of claim 2.

22. The recombinant host cell of claim 21, wherein the host cell is prokaryotic.

23. The recombinant host cell of claim 21, wherein the host cell is a member of a genus selected from *Bacillus, Clostridium, Enterococcus, Geobacillus, Lactobacillus, Lactococcus, Oceanobacillus, Propionibacterium, Staphylococcus, Streptococcus, Streptomyces, Campylobacter, Escherichia, Flavobacterium, Fusobacterium, Helicobacter, Ilyobacter, Neisseria, Pseudomonas, Salmonella*, and *Ureaplasma*.

24. The recombinant host cell of claim 21, wherein the host cell is a member of the *Lactobacillus* genus or *Propionibacterium* genus.

* * * * *

SEQUENCE LISTING

```
<160> NUMBER OF SEQ ID NOS: 8

<210> SEQ ID NO 1
<211> LENGTH: 714
<212> TYPE: DNA
<213> ORGANISM: Bacillus mojavensis

<400> SEQUENCE: 1
atgggaaaag tgctgtcatc gagtaaggaa gccgcggaac tcattcggga ggggataca      60 ctgatcgcgg gcggattcgg cctgtgcgga attcccgagc agctcattct ggcgataagg     120
gataaagggg taaaagattt aaccgtcgtc agcaataatt gcggagttga tgattggggg     180
ctcggtctgc tgctggcaaa caagcaaatc aaaaaaatga tcgcttccta cgtcggagaa     240
aacaaaattt ttgaaaagca attttaagc ggagaattgg aagtggaatt ggttccccaa      300
gggaccctcg ctgaaagaat ccgagccgga ggagcgggta taccgggatt ttacacagcc     360
acaggcgtcg gaacatctat cgctgacggg aaagagcata aaacctttga cggacgcact     420
tatgtgttag aaaaagggat tactggggat gtcgccattg taaaagcatg gaaagcggac     480
accatgggga atttagtttt tcggaaaacg gcaagaaatt tcaatccggt tgccgccatg     540
gcgggaaaga tcacaattgc cgaggcagaa gaaattgttg aggcgggaga gctcgatccc     600
gaccacatac acacgcctgg tatttacgta cagcatgttg tgctcggcac acatgaaaag     660
cggattgaaa aacgaactgt tcagcaagcg gagggaaagg aggcggcaca atga           714

<210> SEQ ID NO 2
<211> LENGTH: 714
<212> TYPE: DNA
<213> ORGANISM: Bacillus mojavensis

<400> SEQUENCE: 2
atggggaaag tcctgtcgtc atccaaagaa gccgcagagt taatccgcga aggtgatacc      60
ctgattgcag gtggctttgg cctgtgtggc atcccggagc agctgatcct ggccatccgt     120
```

-continued

```
gataaggggg ttaaagatct gaccgtagtt tcgaacaatt gtggggttga tgactggggc    180
ttaggcctgt tactgccaa taagcagatc aagaaaatga tcgcgtccta cgtaggggaa     240
aacaaaatct tcgaaaaaca gtttctgtca ggggagttag aagtggaact ggtacctcaa    300
ggtacgctgg cggagcgcat tcgggctggt ggtgcaggca ttcctggctt ttacaccgct    360
acgggtgtag gtacgagtat tgccgatggt aaagaacaca aaacatttga tggtcgtacc    420
tatgtgctgg aaaaaggcat caccggtgat gtagcgatcg ttaaggcttg gaaagctgat    480
acaatgggga acctggtctt tcgtaaaact gcacgcaact tcaatccagt tgcagccatg    540
gcaggcaaaa tcacgatcgc cgaggcggaa gagatcgttg aagcaggcga attagatccg    600
gatcacattc acaccaggca tctatgtg cagcatgtag tcttaggtac ccatgaaaaa      660
cgcatcgaaa aacgcaccgt tcagcaggcc gaagggaaag aagcagccca gtaa          714
```

<210> SEQ ID NO 3
<211> LENGTH: 237
<212> TYPE: PRT
<213> ORGANISM: Bacillus mojavensis

<400> SEQUENCE: 3

```
Met Gly Lys Val Leu Ser Ser Lys Glu Ala Ala Glu Leu Ile Arg
1               5                   10                  15

Glu Gly Asp Thr Leu Ile Ala Gly Gly Phe Gly Leu Cys Gly Ile Pro
                20                  25                  30

Glu Gln Leu Ile Leu Ala Ile Arg Asp Lys Gly Val Lys Asp Leu Thr
            35                  40                  45

Val Val Ser Asn Asn Cys Gly Val Asp Asp Trp Gly Leu Gly Leu Leu
        50                  55                  60

Leu Ala Asn Lys Gln Ile Lys Lys Met Ile Ala Ser Tyr Val Gly Glu
65                  70                  75                  80

Asn Lys Ile Phe Glu Lys Gln Phe Leu Ser Gly Glu Leu Glu Val Glu
                85                  90                  95

Leu Val Pro Gln Gly Thr Leu Ala Glu Arg Ile Arg Ala Gly Gly Ala
            100                 105                 110

Gly Ile Pro Gly Phe Tyr Thr Ala Thr Gly Val Gly Thr Ser Ile Ala
        115                 120                 125

Asp Gly Lys Glu His Lys Thr Phe Asp Gly Arg Thr Tyr Val Leu Glu
130                 135                 140

Lys Gly Ile Thr Gly Asp Val Ala Ile Val Lys Ala Trp Lys Ala Asp
145                 150                 155                 160

Thr Met Gly Asn Leu Val Phe Arg Lys Thr Ala Arg Asn Phe Asn Pro
                165                 170                 175

Val Ala Ala Met Ala Gly Lys Ile Thr Ile Ala Glu Ala Glu Glu Ile
            180                 185                 190

Val Glu Ala Gly Glu Leu Asp Pro Asp His Ile His Thr Pro Gly Ile
        195                 200                 205

Tyr Val Gln His Val Val Leu Gly Thr His Gly Lys Arg Ile Glu Lys
    210                 215                 220

Arg Thr Val Gln Gln Ala Glu Gly Lys Glu Ala Ala Gln
225                 230                 235
```

<210> SEQ ID NO 4
<211> LENGTH: 657
<212> TYPE: DNA
<213> ORGANISM: Bacillus mojavensis

<400> SEQ

```
atgaaggaag ccagaaaacg aatggtcaaa cgtgctgtaa aggaaataaa agacggtatg      60
aacgtcaatc ttgggatagg gatgccgaca cttgtggcaa atgaaatacc ggagggcgtt     120
catgtgatgc ttcaatcaga aaacggcttg cttgggatcg gcccgtatcc gctggacgga     180
acggaagacc cggatctgat caatgcgggg aaagaaacga tcaccgccgt aacaggcgca     240
tcctattttg acagcgcaga atcctttgcg atgatacgag gcggtcatat cgacctggct     300
atcctcgggg gcatggaggt ttctgagcaa ggggatttgg cgaactggat gatcccgggg     360
aaaatggtga agggaatggg cggcgctatg gatttggtca acggggctaa gcgaatcgtt     420
gtcatcatgg agcacgtcaa taaacatggg gaatcgaagg tgaaaaaaca atgctccctc     480
ccgctgacag gacagaaagt cgttcatcgg ctgatcactg atttagctgt ttttgatttt     540
gataacggcc atatgacact gactgagctc caggacggcg tcacgctgga agaggtatat     600
gagaaaactg aagctgactt cgccgtaagc cagtcagtca tccggcaaaa atcttaa       657
```

<210> SEQ ID NO 5
<211> LENGTH: 657
<212> TYPE: DNA
<213> ORGANISM: Bacillus mojavensis

<400> SEQUENCE: 5

```
atgaaagaag cacgcaaacg tatggttaaa cgtgccgtca agaaaatcaa agacgggatg      60
aatgtgaatc tgggcattgg catgccaact ctggtcgcga atgaaattcc ggaaggcgtg     120
cacgttatgt tacagagcga gaacggcctg ctgggtatcg gtccttaccc gctggacggt     180
actgaagatc cggatctgat caatgcaggc aaggagacga tcactgccgt cactggtgcg     240
agctatttcg atagtgcgga atcgttcgcc atgattcgtg gtgggcatat cgacctggcg     300
atcttaggtg gcatggaagt gagtgaacag ggtgacctgg ccaactggat gatcccaggt     360
aagatggtga aggtatgggg aggagccatg gatctggtca acggtgcgaa acgtattgtc     420
gtgattatgg aacatgtgaa caaacacggc gaaagtaaag tcaaaaagca gtgttcactg     480
ccgctgactg ccagaaaagt ggttcaccgc ctgatcaccg acttagccgt ctttgatttt     540
gataacgggc acatgacgct gaccgagctg caggatggcg tcacattgga agaggtgtac     600
gaaaagacag aagccgattt cgcggtgtcc caaagcgtga tccgccaaaa gtcttaa       657
```

<210> SEQ ID NO 6
<211> LENGTH: 218
<212> TYPE: PRT
<213> ORGANISM: Bacillus mojavensis

<400> SEQUENCE: 6

```
Met Lys Glu Ala Arg Lys Arg Met Val Lys Arg Ala Val Lys Glu Ile
1               5                   10                  15

Lys Asp Gly Met Asn Val Asn Leu Gly Ile Gly Met Pro Thr Leu Val
            20                  25                  30

Ala Asn Glu Ile Pro Glu Gly Val His Val Met Leu Gln Ser Glu Asn
        35                  40                  45

Gly Leu Leu Gly Ile Gly Pro Tyr Pro Leu Asp Gly Thr Glu Asp Pro
    50                  55                  60

Asp Leu Ile Asn Ala Gly Lys Glu Thr Ile Thr Ala Val Thr Gly Ala
65                  70                  75                  80

Ser Tyr Phe Asp Ser Ala Glu Ser Phe Ala Met Ile Arg Gly Gly His
                85                  90                  95

Ile Asp Leu Ala Ile Leu Gly Gly Met Glu Val Ser Glu Gln Gly Asp
```

-continued

```
                    100                 105                 110
Leu Ala Asn Trp Met Ile Pro Gly Lys Met Val Lys Gly Met Gly Gly
            115                 120                 125

Ala Met Asp Leu Val Asn Gly Ala Lys Arg Ile Val Val Ile Met Glu
            130                 135                 140

His Val Asn Lys His Gly Glu Ser Lys Val Lys Lys Gln Cys Ser Leu
145                 150                 155                 160

Pro Leu Thr Gly Gln Lys Val Val His Arg Leu Ile Thr Asp Leu Ala
            165                 170                 175

Val Phe Asp Phe Asp Asn Gly His Met Thr Leu Thr Glu Leu Gln Asp
            180                 185                 190

Gly Val Thr Leu Glu Glu Val Tyr Glu Lys Thr Glu Ala Asp Phe Ala
            195                 200                 205

Val Ser Gln Ser Val Ile Arg Gln Lys Ser
            210                 215

<210> SEQ ID NO 7
<211> LENGTH: 29
<212> TYPE: DNA
<213> ORGANISM: Escherichia coli

<400> SEQUENCE: 7
gaagatctat ggtgcaaaac ctttcgcgg                                           29

<210> SEQ ID NO 8
<211> LENGTH: 27
<212> TYPE: DNA
<213> ORGANISM: Escherichia coli

<400> SEQUENCE: 8
aaaagtactc aaccaagtca ttctgag                                             27
```